(12) United States Patent
Brandy et al.

(10) Patent No.: US 9,260,737 B2
(45) Date of Patent: Feb. 16, 2016

(54) RAPID AND SENSITIVE DETECTION OF BACTERIA IN BLOOD PRODUCTS, URINE, AND OTHER FLUIDS

(76) Inventors: Kyle R. Brandy, Rochester, MN (US); Daniel G. Ericson, Rochester, MN (US)

( * ) Notice: Subject to any disclaimer, the term of this patent is extended or adjusted under 35 U.S.C. 154(b) by 148 days.

(21) Appl. No.: 13/572,621

(22) Filed: Aug. 11, 2012

(65) Prior Publication Data
US 2013/0084588 A1    Apr. 4, 2013

Related U.S. Application Data

(60) Provisional application No. 61/574,923, filed on Aug. 11, 2011.

(51) Int. Cl.
*C12Q 1/04*    (2006.01)
*C12Q 1/66*    (2006.01)
*C12Q 1/08*    (2006.01)
*C12Q 1/00*    (2006.01)

(52) U.S. Cl.
CPC  *C12Q 1/04* (2013.01); *C12Q 1/008* (2013.01); *C12Q 1/66* (2013.01)

(58) Field of Classification Search
None
See application file for complete search history.

(56) References Cited

U.S. PATENT DOCUMENTS

| | | | |
|---|---|---|---|
| 6,613,579 B2 | 9/2003 | Wolcott | |
| 6,716,391 B1 | 4/2004 | Olson | |
| 7,419,798 B2 * | 9/2008 | Ericson | 435/34 |
| 2008/0305538 A1 | 12/2008 | Ericson | |
| 2009/0305239 A1 * | 12/2009 | Tawfik et al. | 435/6 |

OTHER PUBLICATIONS

Savitsky, A Plasma Factor for Platelet Adhesiveness and Clot Retraction Acceleration, Blood, 1953, 8: 1091-1098.*
Randak et al., A recombinant polypeptide model of the second nucleotide-binding fold of the cystic fibrosis transmembrane conductance regulator functions as an active ATPase, GRPase and adenylate kinase, FEBS Letters, 410 (1997) 180-186.*
Ford et al, Effect of periodate-oxidized ATP and other nucleotides on firefly luciferase, 1994, Arch Biochem Biophys., 314(2):261-267.*
Morrow JF, Braine HG, Kickler TS, Ness PM, Dick JD, Fuller AK. Septic reactions to platelet transfusions. A persistent problem. *JAMA*. 1991;266(4):555-558.
Barrett BB, Andersen JW, Anderson KC. Strategies for the avoidance of bacterial contamination of blood components. *Transfusion*. 1993;33(3):228-233.
Mitchell K-M T, Brecher ME. 1999. Approaches to the Detection of Bacterial Contamination in Cellular Blood Products. *Transfusion Medicine Reviews* 13:132-144.
Chaney R., et al. 1999. Direct detection of bacteria in cellular blood products using bacterial ribosomal RNA-directed probes coupled to electrochemiluminescence3 *Transfusion Medicine* 9:177-188.
Hanna BA. 1986. Detection of Bacteriaurea by Bioluminescence. *Methods in Enzymology* 133:22-27.
Nilsson LE et al. 1989. Bioluminescent Assay of Bacterial ATP for Rapid Detection of Bacterial Growth in Clinical Blood Cultures. *J. Bioluminescence and Chemiluminescence* 3:101-104.
Stanley PE 1989. A Review of Bioluminescent ATP Techniques in Rapid Microbiology. *J. Bioluminescence and Chemiluminescence* 4:375-380.
Lundin A, Thore A. 1975. Comparison of Methods for Extraction of Bacterial Adenine Nucleotides Determined by Firefly Assay. *Applied Microbiology* 30:713-721.
Lemasters JJ, Hackenbrock CR. 1979. Continuous Measurement of Adenosine Triphosphate with Firefly Luciferase Luminescence. *Meth. Enzymol.* 56:530-544.
Higashi T, et al. 1985. Quantitative and Continuous Analysis of ATP Release from Blood Platelets with Firefly Luciferase Luminescence. *Thrombosis and Haemostasis* 53:65-69.
Blajchman, MA and Golman, MN. 2001. Bacterial contamination of platelet concentrates: incidence, significance, and prevention. Seminars in Hematology. 38 (4 Suppl 11): 20-26.

* cited by examiner

Primary Examiner — Sharmila G. Landau
Assistant Examiner — Stephanie McNeil
(74) Attorney, Agent, or Firm — Hugh McTavish

(57) ABSTRACT

The invention provides methods of detecting bacteria in fluids, including blood, platelets and other blood products for transfusion, and urine. The methods are based on lysing the bacteria to release ATP and detecting the ATP. Eukaryotic cell contamination is a problem to be overcome, because eukaryotic cell contain large amounts of ATP. Thus, some of the methods involve separating intact eukaryotic cells (e.g., platelets) from intact bacterial cells before lysing the bacterial cells to release ATP, contacting the ATP with an ATP-consuming enzyme that catalyzes a reaction, and monitoring the enzyme-catalyzed reaction. Typically, the enzyme is luciferin, and the reaction is monitored by detecting light produced by the luciferin. Other methods of the invention involve contacting a fluid sample with a support surface that binds bacterial cells, lysing the bacterial cells to release ATP, contacting the ATP with an ATP-consuming enzyme, and monitoring the enzyme-catalyzed reaction. Apparatuses for carrying out the methods are also disclosed.

9 Claims, 13 Drawing Sheets

RAPID AND SENSITIVE DETECTION OF BACTERIA IN BLOOD PRODUCTS, URINE, AND OTHER FLUIDS

This application claims priority under 35 U.S.C. 119(e) from U.S. provisional patent application 61/574,923, filed Aug. 11, 2011.

BACKGROUND

Over nine million platelet units are transfused in the United States every year. The platelets are stored at room temperature to prevent loss of function and thus are particularly susceptible to bacterial contamination since any contaminant bacteria can quickly multiply at room temperature. Platelets are often given to cancer chemotherapy patients to treat platelet depletion and the resulting anemia and risk of bleeding caused by chemotherapy. These patients are also immunocompromised and thus at particular risk from bacterial contamination of the platelets. The number of cases of illnesses and death due to contaminated platelets has only recently been gathered.

Bacterial contamination has been the leading cause of transfusion-related deaths over the past three years (1). Bacterial contamination levels as low as $10^2$ to $10^3$ CFU/ml have been associated with fever and positive blood culture. Studies at Johns Hopkins and Dana-Farber revealed rates of sepsis following platelet transfusion from 0.005% to 0.14%, depending on the site and whether the platelets were derived from random donors or single donor apheresis. In the 33,829 transfusions documented, a total of nine cases of sepsis were found (2, 3). The rate of sepsis appears to be lower than the rate of bacterial contamination in studies of platelet purity. It has been widely suggested that the rate of sepsis from platelet transfusion is underreported for a variety of clinical and regulatory reasons.

Because of the risk of sepsis, the FDA requires platelets to be discarded after five days of storage. For a short period (1984-1986) the FDA permitted platelet storage for seven days, but reversed the regulation after data on bacterial proliferation proved troublesome (4).

The available means for testing for bacteria in platelets are too slow, not sensitive enough, or too cumbersome. One method is culturing the growth of microorganisms from the platelets. The BACT/ALERT system uses this approach. However, this requires culturing for one to three days (5). Another method is gram staining of a sample of platelet concentrate for visual microscopic identification of bacteria. But this requires significant labor and was only sensitive to $10^6$ colony forming units (CFU) per ml (5). Acridine orange staining and fluorescence microscopy improved the sensitivity to $10^4$-$10^5$ CFU/ml (5). Visual observation of platelet swirling, or assaying for pH or glucose concentration changes have also been used, but these are not sufficiently sensitive or reliable (5).

A PCR method was used to detect *Yersinia enterocolitica*. This method was quite sensitive, but took six hours and was specific for only one species (5).

Fluorescent antibodies have also been used to detect bacteria with flow cytometry (5). That has the potential to be sensitive, but is expensive and fairly time consuming, and it only detects the species recognized by the antibodies.

Another method of detecting bacteria involved detection of labeled oligonucleotides that hybridize to bacterial rRNA (6). But the process took four hours.

Bacteria have been detected by luminescence detection of bacterial ATP (7, U.S. Pat. No. 3,933,592). Bacteria are lysed to release their ATP, and the ATP is detected by reaction with luciferase and luciferin to produce light. However, eukaryotic cells have far more ATP than bacterial cells, so even a small contamination with eukaryotic cells gives unreliable results. In one method, blood cells were lysed with TRITON X-100, the debris was separated from bacteria by density gradient centrifugation, and the bacterial cell layer of the gradient was extracted, treated to lyse any bacteria, and assayed for ATP by the luciferin-luciferase assay (8).

New methods to detect bacteria in platelets are needed. Preferably, the methods would be inexpensive, fast, detect bacteria of any clinically significant species, and be sensitive, i.e., detect very low numbers of bacteria. New methods of detecting bacteria in other fluids are also needed. These fluids include whole blood for transfusion, whole blood taken from a patient for diagnosis of sepsis, bone marrow stem cells for a bone marrow transplant, serum, plasma, and urine. Rapid detection of bacteria in urine is needed for diagnostic purposes in both human and veterinary medicine.

SUMMARY

The invention provides methods to detect bacteria in platelet concentrate, other blood products for transfusion, blood from a patient assayed for diagnostic purposes, urine, and other fluids. Apparatuses to carry out the methods are also provided. The methods can detect and quantify bacteria in fluids in less than five minutes, allowing detection of bacteria in blood or urine at the bedside or during a clinical visit, and allowing detection of bacteria in platelets or other blood products immediately before they are to be transfused into a patient. The methods are also very sensitive, allowing detection of, in some cases, less than 100 bacterial cells per ml of fluid sample. The methods are not species specific and can be used to quantify any bacteria.

One of the major problems with detecting bacteria in fluids by ATP detection is that most fluids also contain somatic cells or other eukaryotic cells (including platelets), which have large quantities of ATP, masking the smaller amounts of ATP found in bacteria. Some of the methods of the invention involve separating intact eukaryotic cells (including platelets) from intact bacteria prior to lysing the bacteria, to solve the problem of contamination with ATP from the eukaryotic cells. This is done by filtering out the eukaryotic cells with a filter that allows bacterial cells to pass through, or by binding the bacterial cells to a surface that selectively binds bacterial cells and does not bind eukaryotic cells. The binding surface can also serve to concentrate the bacterial cells, increasing the sensitivity of their detection. Alternatively, if a filtration step is used to remove intact eukaryotic cells, the bacterial cells can be concentrated by a second filtration step with a filter that captures the bacteria.

It has also been discovered that eukaryotic cells, including platelets can be adequately separated from bacteria by centrifugation for a time and at a speed such that eukaryotic pellets and bacterial cells remain suspended in the fluid sample, i.e., in the supernatant, in order to assay for bacterial cells by lysing the bacterial cells and detecting ATP.

It has also been discovered that clotting can be used to separate eukaryotic cells, including platelets, from bacterial cells in a blood product containing platelets, in order to assay for bacterial cells by lysing the bacterial cells and detecting ATP.

In addition, it has been discovered that eukaryotic cells, including platelets, can be selectively lysed in a fluid sample without lysing bacterial cells by mixing the fluid sample with an appropriate detergent and sonicating the sample. It has been found that CHAPS specifically, with sonication, allows substantially complete lysis of eukaryotic blood cells with no significant lysis of bacterial cells to allow detection of bacterial cells.

A new method of removing ATP from a mixture before bacterial cells are lysed, so when bacterial cells are lysed the only ATP present is bacterial ATP, is disclosed. An oxidant, for example, sodium periodate, is added. This oxidizatively degrades ATP so that the ATP no longer is biologically active. The periodate can in turn be easily removed by filtration, or can be consumed and inactivated by mixing with a reductant, such as glycerol or glucose. This allows the subsequent lysis of the bacterial cells without the oxidant degrading the bacterial ATP.

Other methods of the invention involve contacting a fluid sample suspected to contain bacteria with a support surface that binds the bacteria, where the contacting step is not necessarily used to separate the bacteria from intact eukaryotic cells. For instance, the eukaryotic cells could be first selectively lysed in the sample, and then the sample contacted with the bacteria-binding surface to concentrate the bacteria and/or remove them from debris and from non-bacterial ATP.

Thus, one embodiment of the invention provides a method of detecting bacteria in a fluid sample suspected of containing bacteria that involves: (a) separating intact eukaryotic cells from intact bacterial cells that may be present in the fluid sample; (b) lysing the bacterial cells to release bacterial ATP into a fluid to generate a bacterial lysate fluid; (c) contacting the bacterial ATP in the bacterial lysate fluid with an ATP-consuming enzyme to generate an ATP assay fluid in which the enzyme catalyzes a reaction; and (d) monitoring the enzyme-catalyzed reaction in the ATP assay fluid.

Another embodiment of the invention provides a method of detecting bacteria in a fluid sample suspected of containing bacteria that involves: (a) contacting the fluid sample with a support surface that binds bacterial cells to concentrate the bacterial cells and/or separate the bacterial cells from other components in the fluid sample; (b) lysing the bacterial cells to release bacterial ATP into a fluid to generate a bacterial lysate fluid; (c) contacting the bacterial ATP in the bacterial lysate fluid with an ATP-consuming enzyme to generate an ATP assay fluid in which the enzyme catalyzes a reaction; and (d) monitoring the enzyme-catalyzed reaction in the ATP assay fluid.

Another embodiment of the invention provides a system for detecting bacteria in a fluid sample that includes: (a) a holding means for receiving a device for separating intact eukaryotic cells from intact bacterial cells in a fluid sample; (b) a fluid-tight material forming an assay chamber adapted to receive fluid flow from the device for separating intact eukaryotic cells from intact bacterial cells in a fluid sample; and (c) a light detector functionally linked to the assay chamber to detect light emitted in the assay chamber.

Another embodiment of the invention provides a system for detecting bacteria in a fluid sample that includes: (a) a holding means for receiving a support surface that binds intact bacterial cells in a fluid sample; (b) a fluid-tight material forming an assay chamber adapted to receive fluid flow from the support surface that binds intact bacterial cells in a fluid sample; and (c) a light detector functionally linked to the assay chamber to detect light emitted in the assay chamber.

Another embodiment of the invention provides a process for preparing a fluid sample suspected of containing bacteria for detecting the bacteria, the process involving: separating intact eukaryotic cells from intact bacterial cells that may be present in the fluid sample to generate a bacterial detection sample that is substantially free of eukaryotic cells for subsequent detection of bacteria in the bacterial detection sample; wherein the detection of bacteria in the bacterial detection sample comprises lysing the bacteria and monitoring ATP released from the lysed bacteria.

The separating intact eukaryotic cells from intact bacterial cells in specific embodiments may be by centrifuging the fluid sample at a speed and for a time such that eukaryotic cells pellet and bacterial cells remain suspended in the fluid sample. The separation is sufficient in some embodiments to allow detection of bacteria by lysis of the remaining cells in the supernatant and detection of ATP from lysed cells, without further separating intact eukaryotic cells from intact bacterial cells (e.g., with a further filtration step).

In another embodiment, the fluid sample is a blood product comprising platelets, and the separating intact eukaryotic cells from intact bacterial cells involves clotting the blood product fluid sample and removing fluid from the clot.

Another embodiment of the invention provides a device adapted to separate eukaryotic cells from intact bacterial cells that may be present in a fluid sample to generate a testing sample to test for bacterial cells. The device comprises: (a) a fluid chamber coupled to (b) a bacteria-separating component selected from (i) a first filter that blocks eukaryotic cells and allows the bacterial cells to pass through coupled to a second filter with a pore size of less than 1 micron that blocks intact bacterial cells, and (ii) a support surface that binds the bacterial cells and does not bind the eukaryotic cells. In use of the device, the fluid sample flows from the fluid chamber through the bacteria-separating component to generate a testing sample containing bacterial cells that may have been present in the fluid sample, wherein the testing sample is substantially free of eukaryotic cells.

Another embodiment of the invention provides an apparatus that includes (a) a port adapted to receive a vessel holding a sample suspected of containing bacterial cells, wherein the vessel comprises (i) a fluid-passable filter and a support surface that binds bacterial cells, or (ii) a fluid-passable filter that has a pore size of less than 1 micron and is impassable to intact bacterial cells. The apparatus also includes (b) a passageway in fluid communication with the port and in fluid communication with (c) an assay chamber. The apparatus also includes (d) a light detector functionally linked to the assay chamber to detect light emitted in the assay chamber; and (e) a pump functionally linked to the passageway and assay chamber and adapted to pump fluid through the passageway and to the assay chamber. The apparatus is adapted to (I) pump a lysing fluid from the passageway through the port and the fluid-passable filter of the vessel when the vessel is received on the port, to lyse bacteria in the vessel and thereby generate a bacterial lysate containing bacterial ATP in the vessel, (II) pump the bacterial lysate from the vessel through the fluid-passable filter of the vessel into the passageway; (III) contact the bacterial ATP in the bacterial lysate with luciferase and luciferin to form an ATP assay fluid; and (IV) monitor light emission from the ATP assay fluid in the assay chamber.

Another embodiment of the invention provides an apparatus for determining the presence or absence of bacteria in a sample suspected of containing bacteria. The apparatus includes: (a) a receptacle means for receiving a sample suspected of containing bacterial cells; linked to (b) a means for lysing the bacterial cells to release bacterial ATP into a fluid to generate a bacterial lysate fluid; linked to (c) a means for contacting the bacterial ATP in the bacterial lysate fluid with an ATP-consuming light-producing enzyme to generate an ATP assay fluid in which the enzyme catalyzes a light-producing reaction; linked to (d) a light-detector means for detecting light produced by the enzyme in the ATP assay fluid.

Another embodiment of the invention provides an apparatus adapted to receive a sample suspected of containing bacterial cells and execute steps comprising:
(a) lysing the bacterial cells to release bacterial ATP into a fluid to generate a bacterial lysate fluid; (b) contacting the bacterial ATP in the bacterial lysate fluid with an ATP-consuming enzyme to generate an ATP assay fluid in which the enzyme catalyzes a reaction; and (c) monitoring the enzyme-catalyzed reaction in the ATP assay fluid.

Another embodiment provides a method of detecting bacteria in a fluid sample containing eukaryotic cells and suspected of containing bacteria, the method comprising: (a) selectively lysing eukaryotic cells in the sample without substantially lysing bacterial cells in the sample by a process comprising mixing a surfactant with the sample to form a surfactant-containing sample, and sonicating the surfactant-containing sample to generate a sonicated sample; (b) consuming ATP in the sonicated sample or removing ATP from the bacterial cells in the sonicated sample; (c) lysing bacterial cells contained in the sonicated sample to release bacterial ATP into a fluid to generate a bacterial lysate fluid; and (d) detecting bacterial ATP in the bacterial lysate fluid.

Another embodiment provides a method of detecting cells in a sample comprising: (a) consuming extracellular ATP in a sample suspected of containing cells by contacting the sample with an oxidizing agent; followed by (b) removing the oxidizing agent from cells in the sample (i) by consuming the oxidizing agent by contacting the oxidizing agent with a reductant or (ii) by separating the cells from the oxidizing agent; (c) lysing cells in the sample to release cellular ATP into a fluid to generate a cell-lysate fluid; and (d) detecting ATP in the cell-lysate fluid.

Another embodiment provides a method of detecting bacteria in a fluid sample suspected of containing bacteria comprising: (a) separating intact eukaryotic cells from intact bacterial cells that may be present in the fluid sample by a process comprising: (i) centrifuging the fluid sample at a speed and for a time such that eukaryotic cells pellet and bacterial cells remain suspended in the fluid sample; or (ii) wherein the fluid sample is a blood product comprising platelets, clotting the blood sample, and removing fluid from the clot; (b) lysing the bacterial cells to release bacterial ATP into a fluid to generate a bacterial lysate fluid; and (c) detecting ATP in the bacterial lysate fluid.

Another embodiment provides a system for detecting cells in a fluid sample comprising: (a) a holding means for receiving a device containing a sample suspected of containing cells; (b) a holding means holding a first fluid reservoir chamber containing an oxidizing solution effective to consume ATP; (c) a fluid-tight material forming an assay chamber adapted to receive fluid flow from the device containing a sample suspected of containing cells; (d) a light detector functionally linked to the assay chamber to detect light emitted in the assay chamber; and (e) a pump functionally coupled to the first fluid reservoir chamber and to the device containing a sample suspected of containing cells, the pump adapted to pump the oxidizing solution from the first fluid reservoir chamber to the device containing a sample suspected of containing cells to consume extracellular ATP in the sample suspected of containing cells.

Another embodiment provides an apparatus adapted to receive a sample suspected of containing cells and execute steps comprising: (a) contacting an oxidizing solution with the sample for a time effective to consume extracellular ATP in the sample; (b) removing the oxidizing agent from cells in the sample (i) by consuming the oxidizing agent by contacting the oxidizing agent with a reductant or (ii) by separating the cells from the oxidizing agent; (c) lysing the cells to release ATP into a fluid to generate a cell lysate fluid; (d) contacting the ATP in the cell lysate fluid with an ATP-consuming enzyme to generate an ATP assay fluid in which the enzyme catalyzes a reaction; and (e) monitoring the enzyme-catalyzed reaction in the ATP assay fluid.

Another embodiment provides a system for detecting bacteria in a fluid sample comprising: (a) a holding means for receiving a vessel containing a sample suspected of containing bacteria; (b) a sonicator adapted to sonicate the sample suspected of containing bacteria in the vessel; (c) a fluid-tight material forming an assay chamber adapted to receive fluid flow from the vessel containing a sample suspected of containing bacteria; and (d) a light detector functionally linked to the assay chamber to detect light emitted in the assay chamber.

Another embodiment provides an apparatus adapted to receive a sample suspected of containing bacterial cells and execute steps comprising: (a) selectively lysing eukaryotic cells in the sample without substantially lysing bacterial cells by a process comprising sonicating the sample, wherein the sample contains a detergent when it is sonicated; (b) consuming extracellular ATP in the sonicated sample or removing extracellular ATP from the bacterial cells in the sonicated sample; (c) lysing the bacterial cells to release bacterial ATP into a fluid to generate a bacterial lysate fluid; (d) contacting the bacterial ATP in the bacterial lysate fluid with an ATP-consuming enzyme to generate an ATP assay fluid in which the enzyme catalyzes a reaction; and (e) monitoring the enzyme-catalyzed reaction in the ATP assay fluid.

Another embodiment of the invention provides an improved optical component in a device for detecting cells (bacterial or eukaryotic). In this embodiment, the assay chamber is placed between a light detector and a concave mirror. Light emitted from the assay chamber that is directed away from the light detector is reflected and focused from the concave mirror back onto the light detector to improve detection. This embodiment of the invention provides a system for detecting cells in a sample comprising: (a) a holding means for receiving a device containing a sample suspected of containing cells; (c) a fluid-tight material forming an assay chamber adapted to receive fluid flow from the device containing a sample suspected of containing cells; (d) a light detector functionally linked to the assay chamber to detect light emitted in the assay chamber; and (e) a concave mirror positioned to reflect light emitted from the assay chamber and concentrate the light onto the light detector.

Another embodiment provide a method of detecting cells in a liquid sample comprising: (a) concentrating cells in a liquid sample and removing the cells from liquid medium of the sample by a process comprising: (i) passing the liquid sample through a filter that blocks the cells; or (ii) contacting the liquid sample with a support surface that binds the cells; or (iii) centrifuging the sample for a time and at a speed sufficient to pellet the cells; (b) contacting the cells removed from the liquid medium with a volume of rich liquid growth medium smaller than the removed liquid medium volume; (c) incubating the cells in the rich liquid growth medium for a time and under conditions effective to amplify the cells; (d) lysing the cells to release cellular ATP into a fluid to generate a cell-lysate fluid; and (e) detecting ATP in the cell-lysate fluid. In this embodiment, it is possible to detect even lower numbers of bacterial or eukaryotic cells. The cells are amplified before detecting them. And by concentrating the cells before placing them in rich medium, the cells are able to get into logarithmic growth faster than and multiply with a shorter doubling time than they could if maintained in a larger volume with a lower concentration of cells.

DETAILED DESCRIPTION

Definitions

Figure 1:
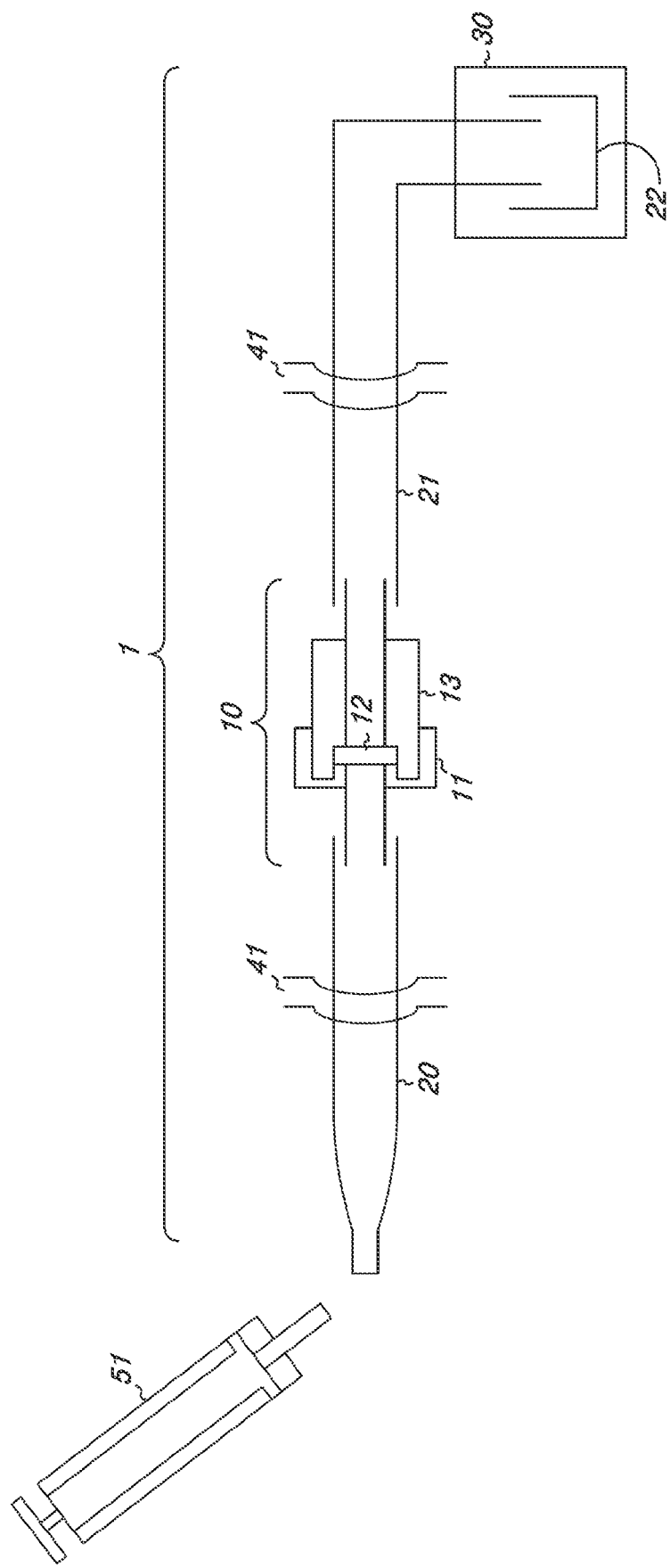
FIG. 1 shows a system of the invention for detecting bacteria in fluids.

The term "eukaryotic cell," as used herein, includes nucleated cells and naturally occurring membrane-enclosed ATP-containing bodies of eukaryotic origin without nuclei, such as platelets, that are suspected to be contained in a fluid.

A "filter," as used herein, is a membrane or device that allows differential passage of particles and molecules based on size. Typically this is accomplished by having pores in the filter of a particular nominal size. For instance, filters of particular interest in this invention have pores sufficiently large to allow passage of bacteria but small enough to prevent passage of platelets or other eukaryotic cells present in the fluid sample of interest. Bacteria are typically smaller than 1 micron in diameter; platelets are approximately 3 microns in diameter; and nucleated eukaryotic cells are typically 10-200 microns in diameter.

The term "platelet concentrate" as used herein refers to a blood fraction enriched in platelets to be used for transfusion into a mammal for the purpose of giving the mammal platelets.

Reference to a support surface that "binds bacteria" means that under the conditions of the contacting, the support surface binds a sufficient fraction of the bacteria present in the fluid to allow detection of the bacteria. Typically, this is at least 50% or at least 90% of the bacteria present in the fluid.

Reference to a support surface that "does not bind eukaryotic cells" means that under the conditions of the contacting used, the binding of eukaryotic cells suspected of being present in the fluid is low enough that the cells are sufficiently removed to not interfere with detection of bacteria that bind to the surface. Typically, under the conditions of the contacting, the support surface binds less than 10%, more preferably less than 1%, more preferably less than 0.1%, of the eukaryotic cells present in the fluid, and most preferably binds an undetectable number of eukaryotic cells.

Reference to a support surface that "does not bind ATP" means that under the conditions of the contacting used, the binding of ATP present in the fluid prior to lysing the bacteria is low enough that the amount of ATP bound does not interfere with detection of bacteria that bind to the surface. Typically, under the conditions of the contacting, the support surface binds less than 10%, more preferably less than 1%, more preferably less than 0.1%, of the ATP present in the fluid, and most preferably binds an undetectable amount of ATP.

DESCRIPTION

Some embodiments of the invention involve separating intact eukaryotic cells (e.g., platelets) from intact bacterial cells before lysing the bacterial cells to release ATP, contacting the ATP with an ATP-consuming enzyme that catalyzes a reaction, and monitoring the enzyme-catalyzed reaction.

The bacteria are lysed to release bacterial ATP into a fluid to generate a bacterial lysate fluid, and the bacterial ATP in the bacterial lysate fluid is contacted with an ATP-consuming enzyme to generate an ATP assay fluid in which the enzyme catalyzes a reaction. In some embodiments, the enzyme is present and able to act in the fluid in which the bacteria are released, so that the bacterial lysate fluid and the ATP assay fluid are the same fluid. In some embodiments, other necessary cofactors such as luciferin are added to the bacterial lysate fluid to allow the enzyme reaction to proceed and form the ATP assay fluid. In some embodiments, the bacterial lysate fluid is contacted with immobilized ATP-consuming enzyme to form the ATP assay fluid. In some embodiments, the bacterial lysate fluid is mixed with a separate fluid containing the ATP-consuming enzyme to form the ATP assay fluid.

In some embodiments, the intact eukaryotic cells include platelets.

In some embodiments, the step of separating intact eukaryotic cells from bacterial cells includes filtering the eukaryotic cells using a filter that blocks the eukaryotic cells and allows the bacterial cells to pass through, to generate a filtered fluid sample containing the bacterial cells.

In some embodiments, the step of separating the intact eukaryotic cells from bacterial cells includes contacting the fluid sample with a support surface that binds the bacterial cells and does not bind the eukaryotic cells.

The support surface typically binds all or almost all types of bacteria. In some embodiments, the support surface binds most species of bacteria. In some embodiments, the support surface binds at least five genera of bacteria. In some embodiments, the support surface binds all of the following species of bacteria: *Bacillus cereus, Bacillus subtilis, Clostridium perfringens, Corynebacterium* species, *Escherichia coli, Enterobacter cloacae, Klebsiella oxytoca, Propionibacterium acnes, Pseudomonas aeruginosa, Salmonella cholerae-*

*suis, Serratia marcesens, Staphylococcus aureus, Staphylococcus epidermidis, Streptococcus pyogenes*, and *Streptococcus viridans.*

Support surfaces that bind bacteria without binding platelets or other eukaryotic cells include surfaces consisting of or containing polycations (e.g., polyethyleneimine or polylysine). Polycations nonspecifically bind the outer surface, i.e., the outer membrane or cell wall, of all or nearly all species of bacteria. Beads that bind bacteria without binding eukaryotic cells including platelets are commercially available from GenPoint (Oslo, Norway). GenPoint BUG TRAP C-version in particular is reported to bind *Acinetobacter, Alcaligenes, Bacillus, Boretella, Borrelia, Chlamydia, Clostridium, Corynebacterium, E. coli, Enterobacter, Haemophilus, Helicobacter, Klebsiella, Listeria, Micrococcus, Mycobacterium, Neisseria, Propionebacterium, Proteus, Pseudomonas, Salmonella, Serratia, Streptococcus, Staphylococcus*, and *Yersinia*.

Binding surfaces that can be used to concentrate bacteria but that also bind platelets or other eukaryotic cells include glass, polyacrylic acid, fibronectin, laminin, collagen, Arg-Gly-Asp oligopeptide, or Phe-His-Arg-Arg-Ile-Lys-Ala (SEQ ID NO:1) oligopeptide. All of those surfaces also nonspecifically bind the outer surface, i.e., the outer membrane or cell wall, of all or nearly all species of bacteria.

In one embodiment, the support surface does not contain an antibody.

In one embodiment, the support surface comprises a plurality of antibodies recognizing a plurality of genera of bacteria. In one embodiment, the support surface comprises a plurality of antibodies that collectively recognize *Bacilus cereus, Bacillus subtilis, Clostridium perfringens, Corynebacterium* species, *Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes*, and *Streptococcus viridans*.

In one embodiment of the methods of the invention, the method involves, after the step of filtering the eukaryotic cells, contacting the filtered fluid sample with a support surface that binds bacteria. The support surface in some embodiments does not bind eukaryotic cells. This provides an additional purification step to back up the filtration of eukaryotic cells. However, since the eukaryotic cells are already filtered from the fluid in these embodiments, in some cases the support surface may bind eukaryotic cells as well as bacterial cells without any harm since eukaryotic cells are not expected to be present in the filtered fluid sample.

In some embodiments of the invention involving a support surface that binds bacteria, the support surface does not bind ATP.

In one embodiment, the step of separating intact eukaryotic cells from intact bacterial cells that may be present in the fluid sample involves before the step of contacting the fluid sample with a support surface that binds the bacteria, filtering the eukaryotic cells from the fluid sample using a filter that blocks the eukaryotic cells and allows the bacterial cells to pass through.

In some embodiments, the bacterial cells are lysed while bound to the support surface to release bacterial ATP into a fluid to generate a bacterial lysate fluid. In other embodiments, the bacterial cells are first eluted from the support surface with an elution fluid, before lysing the bacterial cells to release ATP and generate a bacterial lysate fluid. After elution, the bacterial cells could be lysed immediately, or filtered to concentrate them or bound to another binding surface to concentrate them before lysing the cells.

In particular embodiments, the volume of the ATP assay fluid is smaller than the volume of the fluid sample. That is, the bacterial cells are concentrated before lysis. The method then involves concentrating the bacterial cells prior to the step of lysing the bacterial cells. This improves the sensitivity of the assay and allows detection of a lower concentration of bacterial cells in the fluid sample. In particular embodiments, the volume of the ATP assay fluid is at least 10-fold smaller or at least 100-fold smaller than the volume of the fluid sample. The bacterial cells can be concentrated, specifically, by passing the fluid sample through a filter that blocks passage of intact bacterial cells, or by binding intact bacterial cells to a support surface.

The bacterial cells can be lysed by various methods. These include heat (e.g., to 100° C. or above) or contact with detergents, or a combination of the two. Other methods include contact with acid or base. Trichloroacetic acid and perchloric acid, and probably other acids, have the advantage of denaturing bacterial apyrase, which otherwise can hydrolyze the released ATP (9, 10). Bacterial cells can also be lysed by sonication, contact with particles (e.g., glass beads), freeze-thaw, organic solvents (e.g., chloroform, phenol, or n-butanol), enzymes (e.g., lysozyme), or french press. Combinations of two or more of the above lysing methods or agents may also be used.

If acid or base is used to lyse the bacterial cells, the pH may need to be adjusted after the lysis step before adding, or simultaneously with adding, luciferase or another ATP-consuming enzyme used in the assay in order for the enzyme to work. Luciferase also requires $Mg^{2+}$ as a cofactor, so this may need to be added. Exposure to $O_2$ is also necessary. The luciferase reaction is shown below, where E is luciferase and $LH_2$ is luciferin.

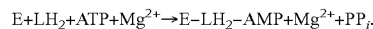

$$E+LH_2+ATP+Mg^{2+} \rightarrow E-LH_2-AMP+Mg^{2+}+PP_i.$$

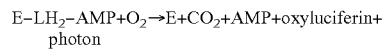

$$E-LH_2-AMP+O_2 \rightarrow E+CO_2+AMP+oxyluciferin+photon$$

The light is detected as an indication of ATP concentration. Provided excess luciferin and luciferase are present, the rate of reaction is proportional to ATP concentration. Because the overall forward reaction is strongly favored, in the absence of significant inhibitors the total light generated, as well as the reaction rate, is proportional to ATP concentration. A correlation between light intensity and ATP concentration has been shown over a 1000-fold range of ATP concentration. The overall reaction can occur very rapidly, with reaction times less than 500 msec demonstrated (16).

Oxyluciferin is a powerful non-competitive inhibitor of the luciferase reaction. With a half-saturation constant of 0.23 µM, even at very low ATP concentrations the buildup of oxyluciferin can result in a rapid decay in luminescence (17).

Some lysis agents, including trichloroacetic acid, may somewhat decrease the light signal from the luciferase reaction. The amount of inhibition can be determined by assays, and in some cases can be reversed by, e.g., for TCA, neutralization of the acid following lysis.

In particular embodiments, the step of monitoring the enzyme-catalyzed reaction involves monitoring a product produced by the reaction.

In preferred embodiments, the product is light.

In preferred embodiments where the product monitored is light, the enzyme is luciferase and the method involves contacting the bacterial ATP with luciferase and luciferin.

In particular embodiments, the fluid sample is a bodily fluid of a mammal, e.g., blood, spinal fluid, urine, or a blood product such as platelet concentrate.

In particular embodiments, the blood product is whole blood, serum, plasma, bone marrow stem cell concentrate, or erythrocyte concentrate.

In one embodiment, the bodily fluid is urine. In another embodiment, the bodily fluid is spinal fluid.

In particular embodiments, the bodily fluid is for transfusion into a mammal.

One of the advantages of the invention is that it gives good sensitivity of detection of bacteria. In particular embodiments, the methods detect at least three bacterial genera at a level of 10,000, 1,000, or 100 bacterial colony forming units (CFU) per ml of the fluid sample.

In particular embodiments, the methods detect 10,000 CFU per ml of each of the following species of bacteria: *Bacillus cereus, Bacillus subtilis, Clostridium perfringens, Corynebacterium* species, *Escherichia coli, Enterobacter cloacae, Klebsiella oxytoca, Propionibacterium acnes, Pseudomonas aeruginosa, Salmonella choleraesuis, Serratia marcesens, Staphylococcus aureus, Staphylococcus epidermidis, Streptococcus pyogenes,* and *Streptococcus viridans*. In other particular embodiments, the methods detect 1,000 CFU per ml of each of those species, or 100 CFU per ml of each of those species.

In particular embodiments of the filter used to block eukaryotic cells and allow bacterial cells to pass through, the filter has a pore size of 1-10 microns, 2-10 microns, or 4-10 microns. In other particular embodiments, the filter has a pore size of about 1 micron, about 2 microns, 1-3 microns, 1-5 microns, about 5 microns, or about 10 microns.

One embodiment of the invention provides a method of detecting bacteria in a fluid sample suspected of containing bacteria that involves: (a) contacting the fluid sample with a support surface that binds bacterial cells to concentrate the bacterial cells and/or separate the bacterial cells from other components in the fluid sample; (b) lysing the bacterial cells to release bacterial ATP; (c) contacting the bacterial ATP with an ATP-consuming enzyme that catalyzes a reaction; and (d) monitoring the enzyme-catalyzed reaction.

A particular embodiment of that method includes, before the step of contacting the fluid sample with a support surface that binds bacterial cells, selectively lysing eukaryotic cells that may be present in the fluid sample without substantially lysing bacterial cells that may be present in the fluid sample. TRITON-X-100, for instance, at room temperature, neutral pH, and appropriate concentrations, lyses platelets and other somatic cells without lysing bacteria.

Contacting the fluid with a support surface that binds bacterial cells after selectively lysing the eukaryotic cells can separate the bacterial cells from eukaryotic cell enzymes and debris that might interfere with assaying bacterial ATP, provided the relevant eukaryotic cell enzymes and debris do not bind to the bacteria-binding surface. In particular, it is advantageous if the bacteria-binding surface does not bind ATP, since that background ATP can interfere with assay of the ATP released with lysis of the bacterial cells. It can also be advantageous for the bacteria-binding surface to not bind apyrase released from the lysed eukaryotic cells, since apyrase would hydrolyze the bacterial ATP when it is released.

In particular embodiments of the method involving contacting the fluid sample with a support surface that binds bacteria, the method involves before the step of contacting the support surface, filtering intact eukaryotic cells that may be present in the fluid sample from the fluid sample using a filter that blocks the eukaryotic cells and allows the bacterial cells to pass through.

In particular embodiments, the support surface binds bacterial cells and does not bind eukaryotic cells. In other embodiments, it binds both bacterial and eukaryotic cells.

In particular embodiments of the methods of detecting bacteria, the fluid sample assayed that is suspected of containing bacteria is less than 5 ml.

In particular embodiments, the steps of (i) lysing the bacterial cells to release bacterial ATP into a fluid to generate a bacterial lysate fluid; (ii) contacting the bacterial ATP in the bacterial lysate fluid with an ATP-consuming enzyme to generate an ATP assay fluid in which the enzyme catalyzes a reaction; and (iii) monitoring the enzyme-catalyzed reaction in the ATP assay fluid are automated. In other embodiments, the step of separating intact eukaryotic cells from intact bacterial cells that may be present in the fluid sample is also automated.

In specific embodiments, the automated steps of lysing, contacting, and monitoring that are referred to in the previous paragraph are completed in less than 5 or less than 2 minutes. In a particular embodiment where the step of separating intact eukaryotic cells from intact bacterial cells is also automated, that step and the steps of lysing, contacting, and monitoring are all completed in less than 5 or less than 2 minutes.

Another embodiment of the invention provides a process for preparing a fluid sample suspected of containing bacteria for detecting the bacteria, the process involving: separating intact eukaryotic cells from intact bacterial cells that may be present in the fluid sample to generate a bacterial detection sample that is substantially free of eukaryotic cells for subsequent detection of bacteria in the bacterial detection sample; wherein the detection of bacteria in the bacterial detection sample comprises lysing the bacteria and monitoring ATP released from the lysed bacteria.

In a particular embodiment, the step of separating intact eukaryotic cells from intact bacterial cells involves filtering the eukaryotic cells using a filter that blocks the eukaryotic cells and allows the bacterial cells to pass through.

In a more specific embodiment, the process involves, after filtering the eukaryotic cells, concentrating the intact bacterial cells in the fluid sample.

In another embodiment, the step of separating intact eukaryotic cells from intact bacterial cells involves contacting the fluid sample with a support surface that binds the bacterial cells and does not bind the eukaryotic cells.

The separating intact eukaryotic cells from intact bacterial cells in specific embodiments may be by centrifuging the fluid sample at a speed and for a time such that eukaryotic cells substantially pellet and bacterial cells remain suspended in the fluid sample. With whole blood, it has been found that centrifuging at 130×g for 8 minutes or 5,000×g for 15 seconds successfully removed eukaryotic cells, including platelets, to allow detection of 10,000 cfu per ml of bacteria.

In another embodiment, the fluid sample is a blood product comprising platelets, and the separating intact eukaryotic cells from intact bacterial cells involves clotting the blood product fluid sample and removing fluid from the clot.

Clotting can be accomplished by adding thrombin to the sample to begin the clotting cascade. It can be by adding other chemicals or clotting factors to begin the clotting cascade, such as collagen, ADP, or arachidonic acid. Clotting can also be initiated by physical means, such as passing a fluid blood product through narrow passageways to create shear forces or stirring to create shear forces that initiate clotting.

Some agents, such as ADP, collagen, epinephrine, and arachidonic acid, work to clump platelets without forming a complete blood clot with coagulation proteins. Other agents, such as thrombin, form a blood clot that includes coagulation proteins as well as platelets. Either method can be used. If a blood clot that includes coagulation proteins is formed, it is desirable to force fluid from the clot by squeezing or filtering the clot, since the released fluidic portion includes bacteria that are otherwise contained in the clot. Thus, the terms "clot" or "clotting" as used herein include clumping platelets with or without formation of fibrin from fibrinogen and entrapment of other blood cells with coagulation proteins.

After or before separating eukaryotic cells from prokaryotic cells by one of these methods, one or more additional methods to separate eukaryotic cells from prokaryotic cells can be used. For example, in addition to centrifugation or clotting, filtration or binding to a support surface that binds bacteria and does not bind eukaryotic cells can be used.

Another embodiment provides a method of detecting bacteria in a fluid sample containing eukaryotic cells and suspected of containing bacteria, the method comprising: (a) selectively lysing eukaryotic cells in the sample without lysing bacterial cells in the sample by a process comprising mixing a surfactant with the sample to form a surfactant-containing sample, and sonicating the surfactant-containing sample to generate a sonicated sample; (b) consuming ATP in the sonicated sample or removing ATP from the bacterial cells in the sonicated sample; (c) lysing bacterial cells contained in the sonicated sample to release bacterial ATP into a fluid to generate a bacterial lysate fluid; and (d) detecting bacterial ATP in the bacterial lysate fluid.

It has been found that eukaryotic blood cells can be selectively lysed in a mixture with bacteria by mixing the detergent CHAPS at 0.25% final concentration (w/v) and sonicating the sample 40 kHz ultrasound for 60 seconds. One ml platelet concentrate was mixed with 3 ml water and CHAPS to a final concentration of 0.25% (w/v). The mixture was sonicated for 60 seconds at 40 kHz ultrasound. The sample was then passed through a 0.2 micron pore size filter to trap and concentrate bacteria. 5 ml of 25 mM $NaIO_4$ was passed through the filter at a rate of 0.6 ml per second to consume eukaryotic ATP. Then 5 ml of 0.5 M glucose was passed through the filter to consume the periodate. Then BAC-TITER GLO reagent (Promega, Madison, Wis.), which contains luciferin, luciferase, and detergent that lyses bacteria, is added to lyse bacteria and release ATP to react with luicferin and luciferase. By this procedure, which does not involve separating intact eukaryotic cells from intact bacterial cells, e.g., by filtration, bacterial concentrations of less than 10,000 cfu per ml were detected.

In specific embodiments of selectively lysing eukaryotic cells in the sample without substantially lysing bacterial cells in the sample by a process comprising mixing a surfactant with the sample to form a surfactant-containing sample, and sonicating the surfactant-containing sample to generate a sonicated sample, the surfactant is CHAPS. In other embodiments it is a CHAPS detergent. This is the family of zwitterionic detergents with structures similar to CHAPS. These include CHAPS, CHAPSO, BigCHAP, and deoxy BigCHAP.

CHAPS is a zwitterionic detergent. In other embodiments, the surfactant is a zwitterionic detergent. These include, in addition to CHAPS family detergents, ZWITTERGENTS.

Surfactants or other lysis agents, such as ammonium chloride, can be used instead without sonication to selectively lyse bacteria. CHAPS without sonication has been found by us to selectively lyse blood cells without sonication, but more complete lysis is achieved with sonication. Other detergents at certain concentrations, such as 0.1% TRITON X-100, can also be used to selectively lyse eukaryotic cells without sonication. In some cases, however, the lysis of eukaryotic cells may not be complete. In that situation, a separate step to separate intact eukaryotic cells from intact bacterial cells may be added. The separation of intact eukaryotic cells from intact bacterial cells can be before the selective lysis or after it.

A new method of removing ATP from a mixture before bacterial cells are lysed, so when bacterial cells are lysed the only ATP present is bacterial ATP, is disclosed. An oxidant, for example, sodium periodate, is added. This oxidizatively degrades ATP so that the ATP no longer is biologically active. The periodate in turn can be easily removed by filtration, or can be consumed and inactivated by mixing with a reductant, such as glycerol or glucose. This allows the subsequent lysis of the bacterial cells without the oxidant degrading the bacterial ATP.

Another embodiment provides a method of detecting cells in a sample comprising: (a) consuming extracellular ATP in a sample suspected of containing cells by contacting the sample with an oxidizing agent; followed by (b) removing the oxidizing agent from cells in the sample (i) by consuming the oxidizing agent by contacting the oxidizing agent with a reductant or (ii) by separating the cells from the oxidizing agent; (c) lysing cells in the sample to release cellular ATP into a fluid to generate a cell-lysate fluid; and (d) detecting ATP in the cell-lysate fluid.

Contaminating ATP can be a problem in attempting to detect cells of any sort, either eukaryotic or prokaryotic. The method of using an oxidant to consume the contaminating ATP before lysing cells is simpler than enzymatic methods, because the oxidant can be easily removed, e.g., by filtering it away from cells, or easily consumed with a reductant after it has reacted with any contaminating ATP.

In other embodiments of detecting intact living cells (which can be either eukaryotic cells or bacterial cells) the intact living cells are immobilized by binding to a solid surface or by being trapped on a filter, and contaminating extracellular ATP is washed away with water or aqueous solution that does not contain an oxidant, before lysing the cells and detecting ATP from the lysed cells.

One embodiment of the invention provides a system for detecting bacteria in a fluid sample that includes: (a) a holding means for receiving a device for separating intact eukaryotic cells from intact bacterial cells in a fluid sample; (b) a fluid-tight material forming an assay chamber adapted to receive fluid flow from the device for separating intact eukaryotic cells from intact bacterial cells in a fluid sample; and (c) a light detector functionally linked to the assay chamber to detect light emitted in the assay chamber.

One embodiment of the system is depicted in FIG. 1. The system 1 includes filtering device 10, containing a filter 12 held in place between two interlocking pieces 11 and 13, is used to filter out intact eukaryotic cells, allowing intact bacterial cells to pass through the device. The filter is held in place by attachment to the ends of tubing sections 20 and 21, with clips 41 holding the tubing sections in place. Syringe 51 can be used to project a fluid sample into the system, forcing it through tubing section 20, filter device 10, tubing section 21, and into assay chamber 22. After lysing intact bacterial cells, ATP in the assay chamber is reacted with luciferin and luciferase to produce light. The light is detected by light detector 30. The light detector can be any suitable device that detects light, including a photomultiplier tube or a photodiode.

Other means for holding the device for separating intact eukaryotic cells from intact bacterial cells 10 can include a clip or receptacle or the like that directly holds the device in place.

Figure 2:
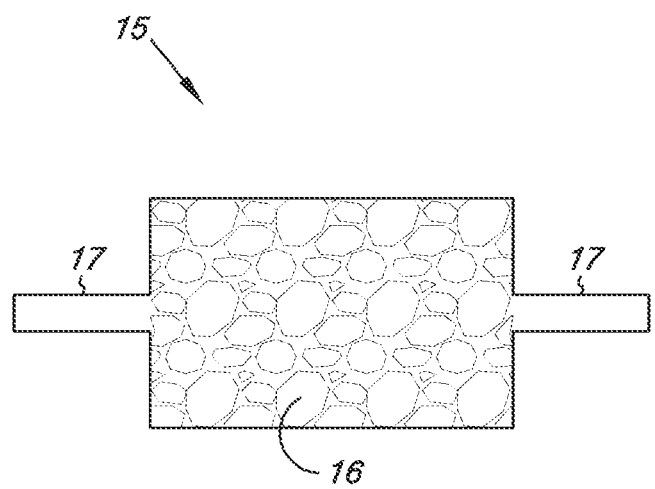
FIG. 2 shows a device for separating intact eukaryotic cells from intact bacterial cells by means of a support surface that binds bacterial cells.

In place of filter device 10, the system can include a device 15 containing a support surface that binds bacteria and does not bind eukaryotic cells. FIG. 2 shows such a device 15, with beads 16 having the bacteria-binding support surface, and ports 17 adapted for engagement with the ends of tubing sections 20 and 21 in FIG. 1. When a fluid sample passes through the device, intact bacterial cells are bound and intact eukaryotic cells pass through and are separated.

In some embodiments, the system includes the device for separating intact eukaryotic cells from intact bacterial cells in the holding means for the device.

Figure 3:
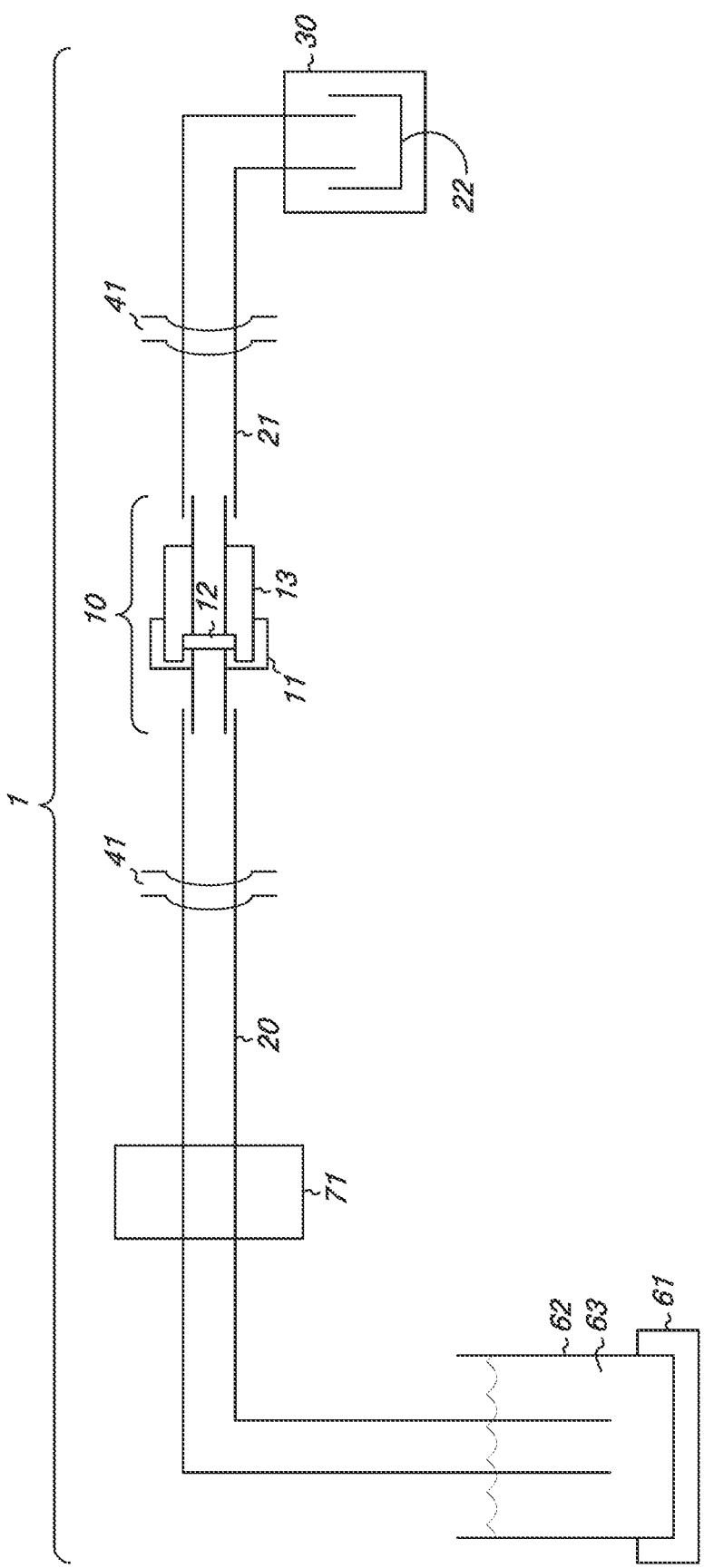
FIG. 3 shows another system of the invention for detecting bacteria in fluids.

In some embodiments of the system, the system includes (d) a holding means for receiving a fluid sample reservoir in fluid communication with the device for separating intact eukaryotic cells from intact bacterial cells; and (e) a pump functionally coupled to the fluid sample reservoir, the device for separating intact eukaryotic cells from intact bacterial cells (separation device), and the assay chamber, to pump fluid from the fluid-sample reservoir to the separation device and from the separation device to the assay chamber. Such a system is shown in FIG. 3. Sample reservoir 62 held on receptacle 61, and holding fluid sample 63 is shown, together with pump 71 for pumping fluid from the sample reservoir to the separation device 10 and the assay chamber 22.

In some embodiments, the assay chamber contains luciferase. For instance, luciferase may be able to be immobilized in the wall of the assay chamber or on beads in the assay chamber. Or luciferase can be added as a solution to the assay chamber.

Figure 4:
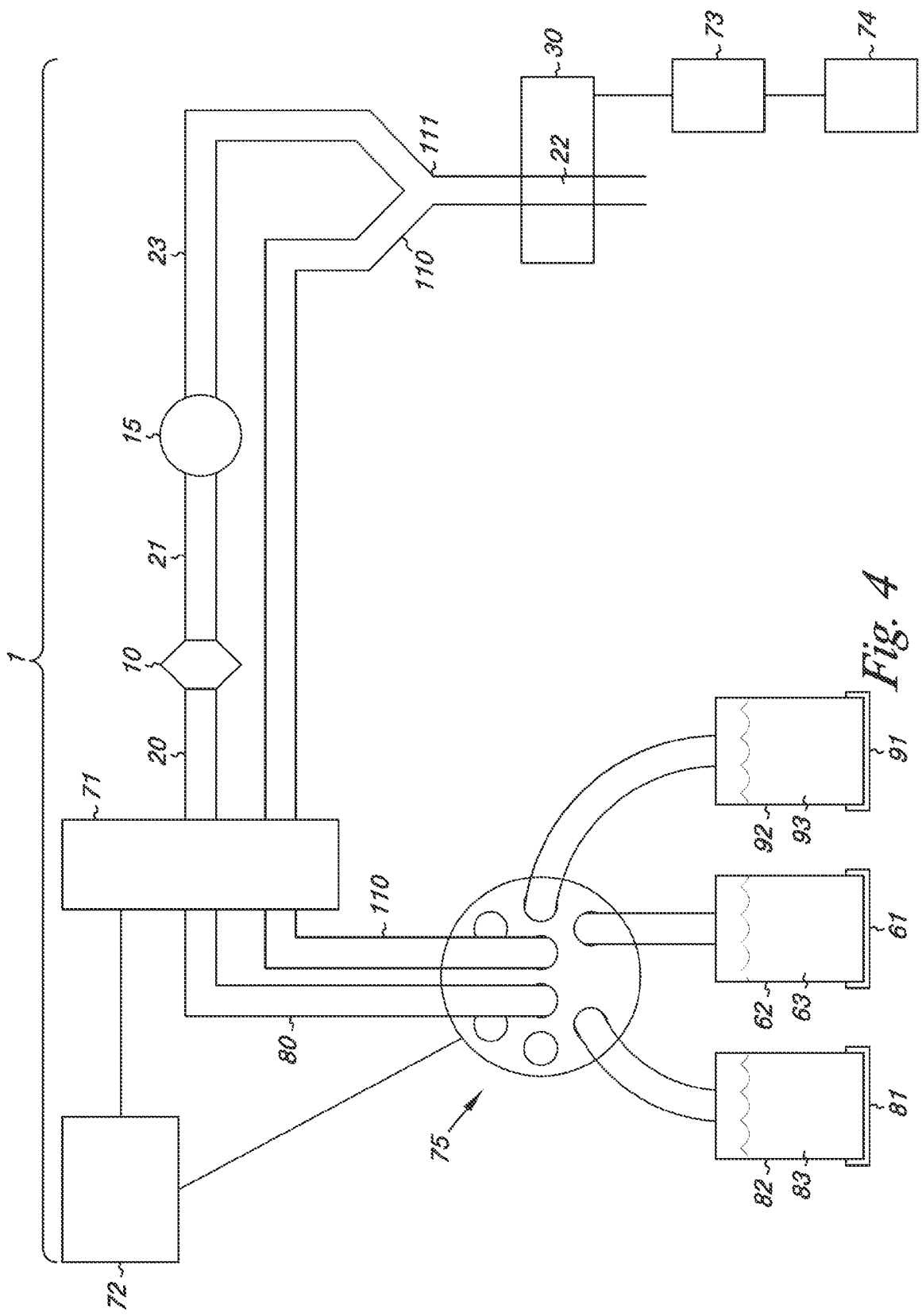
FIG. 4 shows another system of the invention for detecting bacteria in fluids.

FIG. 4 shows several features that are included in some embodiments of the systems of the invention. The system includes a fluid sample reservoir 62 held in a holding means 61 and containing a fluid sample 63 to be assayed for bacteria. The system of FIG. 4 also includes a wash solution reservoir 82 held in a holding means 81 and containing a wash solution 83. A luciferase solution reservoir 92 held by a holding means 91 and containing a luciferase solution 93 is also shown. The solutions held in the reservoirs are linked to a multiport selection valve 75, which outputs the appropriate solution pumped by pump 71 to passages 20 or 110. Initially, the fluid sample is pumped through passage 20 to filter device 10, where eukaryotic cells are filtered out, and on to device 15 containing a support surface that binds bacteria. Bacteria in the fluid sample are bound to the support surface. The wash solution 83 is then pumped through passageways 20 and 21 to the bacteria-binding device 15. If the wash solution contains a lysing agent, the wash solution lyses the bacteria bound in device 15, releasing ATP into a bacterial lysate fluid that is carried out into passageway 23.

A luciferase solution 93 can be pumped into passageway 110 with the multiport selection valve and the pump. The multiport selection valve 75 and pump 71 can be controlled by a processor 72. At Y junction 111, the luciferase solution and the bacterial lysate fluid are mixed to form an ATP assay fluid, which is transported into assay chamber 22, which in FIG. 4 is shown as a flow-through cell. Light emitted in the assay chamber is detected by the light detector 30.

A display 74 may be functionally linked to the light detector 30 for displaying raw or processed data from the light detector. In some embodiments, the system contains a processor 73 linked to the detector that processes data from the detector.

Figure 5:
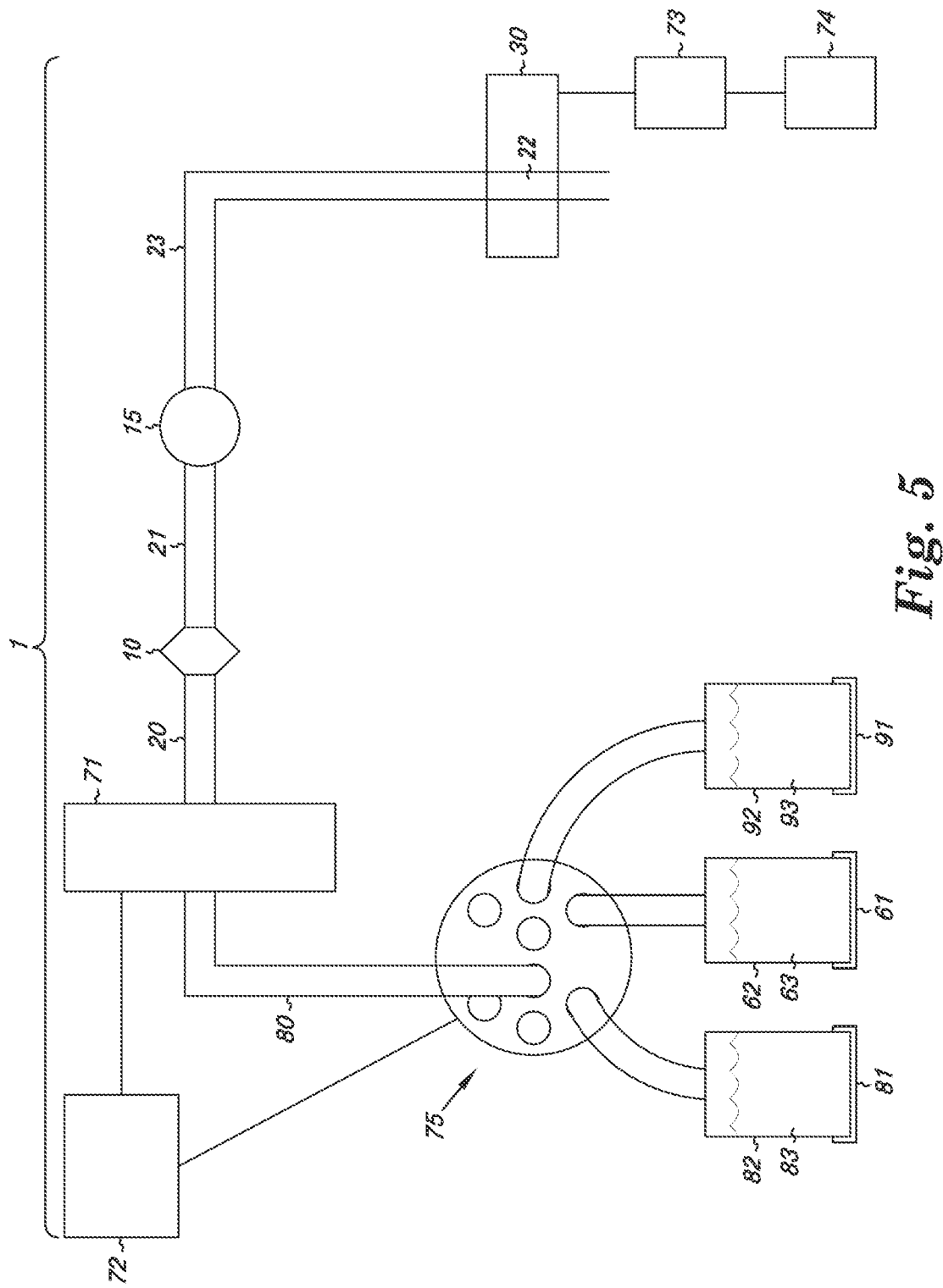
FIG. 5 shows another system of the invention for detecting bacteria in fluids.
Figure 6:
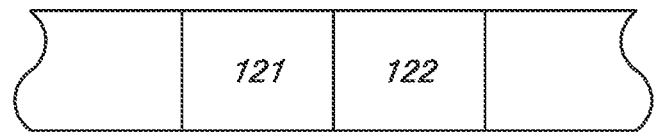
FIG. 6 shows tubing having two stacked zones of fluids.

It is also possible to have a system as shown in FIG. 5 with only one passageway emerging from the multiport selection device. Here, in some embodiments, if a wash solution containing a lysing agent and a luciferase solution are used, the solutions can be pumped through the passageways as stacked zones for mixing and analysis by sequential injection analysis (SIA) (11-15). Stacked fluid zones, such as 121 and 122 are produced in narrow bore tubing as shown in FIG. 6. One zone may contain bacterial ATP and another luciferase. The zones can be transported as adjacent unmixed zones into the assay chamber 22. Rapid bidirectional flow or unidirectional flow past a barrier such as a frit can mix the zones. Optionally, the stacked fluid zones can be separated by gas bubbles.

Upon mixing, the luciferase-catalyzed reaction produces light, which is detected by the detector. SIA is one mechanism for the luciferase to be contacted with the ATP in the assay chamber and in front of the detector, so that there is no delay between mixing of the ATP with the luciferase and flow of the assay solution into the detector. The light-producing luciferase reaction can decay rapidly, so it is advantageous to mix luciferase with the ATP in the assay chamber so there is no delay between mixing the ATP and the luciferase and detecting the reaction. This increases the sensitivity of the method. Other means of making the initial contact of ATP with luciferase in or immediately before the assay chamber are also possible. The luciferase solution can be mixed with the ATP-containing bacterial lysate fluid by connecting flows of the luciferase solution and the bacterial lysate fluid at a Y connection 111 immediately before the assay chamber as shown in FIG. 4. The luciferase can be immobilized in the assay chamber, e.g., on the walls of the assay chamber, so that the ATP of the bacterial lysate fluid initially contacts the luciferase in the assay chamber. Or a luciferase solution and an ATP-containing bacterial lysate fluid can be added separately to an assay chamber of the type shown in FIG. 1 and mixed in the assay chamber to form the ATP assay fluid.

But it has been found that the decay time of the luciferase reaction is long enough that luciferase can be contacted with the ATP from the lysed bacteria up to about 5 or even about 10 minutes before detecting light emission. However, the less of a time delay there is, the more sensitive bacterial detection will be.

In FIG. 4 and FIG. 5, the wash solution 83 can be an oxidizing solution effective to consume ATP. The oxidizing solution, for instance, can be a sodium periodate solution. A solution of 25 mM $NaIO_4$ has been found to be effective to consume ATP. The oxidant is believed to act by oxidizing the purine ring system of ATP, not by hydrolyzing the phosphate bonds.

Sequential injection analysis with narrow tubing has the advantage of minimizing the volumes of fluids consumed in the assay for bacteria and bacterial ATP. Both the volume of sample fluid and the volume of other reagents, such as luciferase, consumed can be minimized.

Some embodiments of the systems of the invention include a device for concentrating intact bacterial cells in fluid communication between the device for separating intact eukaryotic cells from intact bacterial cells and the assay chamber. The device for concentrating intact bacterial cells can involve, for instance, a support surface that binds bacterial cells or a filter that blocks passage of bacterial cells. Such an embodiment is shown in FIG. 4, where device 15 includes a bacteria-binding support surface.

Some embodiments of the systems of the invention include (d) a holding means for receiving a fluid sample reservoir in fluid communication with the device for separating intact eukaryotic cells from intact bacterial cells; (e) a pump functionally coupled to the fluid sample reservoir, the device for separating intact eukaryotic cells from intact bacterial cells (separation device), and the assay chamber, to pump fluid from the fluid-sample reservoir to the separation device, and from the separation device to the assay chamber; (f) a holding means for receiving a wash solution reservoir; and (g) a multiport selection valve in fluid communication with the device for separating intact eukaryotic cells from intact bacterial cells, the assay chamber, the fluid sample reservoir, and the wash solution reservoir, the multiport selection valve adapted for transmitting fluid from the fluid sample reservoir in one position and from the wash solution reservoir in another position.

In some embodiments, a processor is operably coupled to the pump and the multiport selection valve and programmed to deliver a predetermined volume of fluid from the fluid sample reservoir to the separation device, from the separation device to the assay chamber, and from the wash solution reservoir to the assay chamber.

One embodiment of the invention provides a system for detecting bacteria in a fluid sample that includes: (a) a holding means for receiving a support surface that binds intact bacterial cells in a fluid sample; (b) a fluid-tight material forming an assay chamber adapted to receive fluid flow from the support surface that binds intact bacterial cells in a fluid sample; and (c) a light detector functionally linked to the assay chamber to detect light emitted in the assay chamber.

In particular embodiments, the system includes in the holding means (a) the support surface that binds intact bacterial cells.

In a particular embodiment, the support surface does not bind ATP. This has the advantage that ATP present before the bacteria are lysed (i.e., potentially non-bacterial ATP) is separated from the intact bacteria and therefore separated from the bacterial ATP released when the bacteria are lysed.

In another particular embodiment, the support surface does not bind intact eukaryotic cells that may be present in the fluid sample.

In other embodiments, the support surface does bind intact eukaryotic cells. Contamination by eukaryotic ATP in these embodiments can be avoided by selectively lysing the eukaryotic cells before or after the fluid sample is contacted with the support surface, or otherwise removing the eukaryotic cells, e.g., by filtration, before or after the fluid sample is contacted with the support surface.

Another embodiment of the invention provides an apparatus adapted to receive a sample suspected of containing bacterial cells and execute steps comprising: (a) lysing the bacterial cells to release bacterial ATP into a fluid to generate a bacterial lysate fluid; (b) contacting the bacterial ATP in the bacterial lysate fluid with an ATP-consuming enzyme to generate an ATP assay fluid in which the enzyme catalyzes a reaction; and (c) monitoring the enzyme-catalyzed reaction in the ATP assay fluid.

In a particular embodiment, the sample suspected of containing bacterial cells is a fluid sample and the apparatus executes the further step of separating intact eukaryotic cells from intact bacterial cells that may be present in the fluid sample before the step of lysing the bacterial cells.

In a particular embodiment, the bacterial lysate fluid and the ATP assay fluid are each less than 1 ml.

In a particular embodiment, the apparatus executes steps (a), (b), and (c) in less than 2 minutes.

Figure 7:
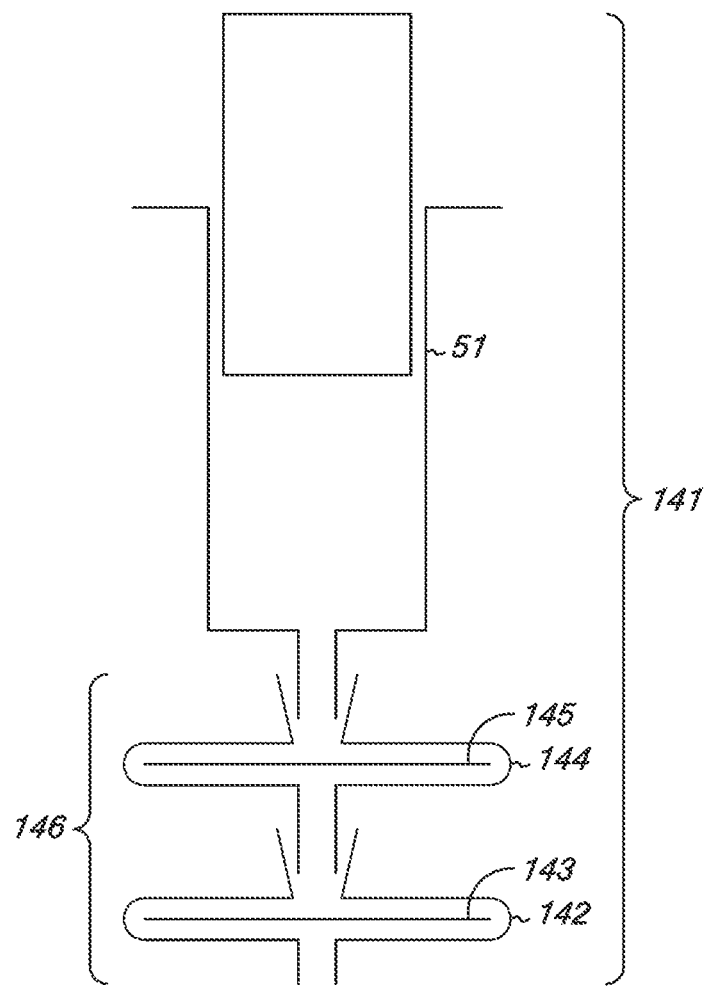
FIG. 7 shows a device for separating eukaryotic cells from intact bacterial cells that may be present in a fluid sample to generate a testing sample to test for bacterial cells.

An example of another embodiment of the invention is shown in FIG. 7. FIG. 7 shows a device 141 for separating eukaryotic cells from intact bacterial cells that may be present in a fluid sample to generate a testing sample to test for bacterial cells. The device 141 includes a fluid chamber 51 that in this example is a syringe. The syringe 51 is coupled to a bacteria-separating component 146 that includes a first filter 145 that blocks eukaryotic cells and allows the bacterial cells to pass through coupled to a second filter 143 with a pore size of less than 1 micron that blocks intact bacterial cells. The filters 145 and 143 in FIG. 7 are held in filter devices 144 and 142. The filter devices include male and female luer lock ends allowing the devices to be interlocked. The syringe 51 also has a luer lock fitting, allowing it to lock to the first filter device 144. Thus, the syringe is used to pump the fluid sample through the first filter 145 with a pore size in one embodiment of 5 microns. This blocks eukaryotic cells including platelets, but allows bacteria through. The second filter 143 has a pore size that blocks bacteria, allowing the bacteria to be concentrated on the outer surface of this second filter. Thus, the device generates a testing sample containing bacterial cells that may have been present in the fluid sample, wherein the testing sample is substantially free of eukaryotic cells.

In another embodiment of the device for separating intact eukaryotic cells from intact bacterial cells to generate a testing sample, the bacteria-separating component is a first filter that blocks eukaryotic cells and allows the bacterial cells to pass through coupled to a second filter with a pore size of less than 1 micron that blocks intact bacterial cells. In a particular embodiment, the first filter has a pore size of 1-10 microns. Filters with 2.0, 3.0, and 5.0 micron nominal pore sizes have been used to successfully block intact eukaryotic cells, including platelets, and allow bacterial cells to pass through. Filters with a nominal pore size of 0.45 and 0.2 micron have been used to block and concentrate intact bacterial cells.

In another embodiment, the bacteria-separating component is the combination of a first filter that blocks eukaryotic cells and a second filter that blocks bacterial cells, and the device includes beads having a support surface that binds bacterial cells, where the beads are held between the first and second filters. Where beads that bind bacteria are held between two filters in the device, in another embodiment, the second filter has a larger pore size such that it does not itself block bacteria but retains the beads that bind bacteria. The second filter in this embodiment could be the same filter type as the first filter.

In another embodiment of the device, the bacteria-separating component is a support surface that binds the bacterial cells and does not bind the eukaryotic cells. For instance, the bacteria-separating component could be beads having a surface that binds bacterial cells and does not bind eukaryotic cells. The beads could be held between two filters. At least the first filter would have to have a pore size large enough to allow bacteria to pass. The filters could be filters having a pore size large enough to also permit eukaryotic cells to pass, but small enough to block the beads. The filters could, for instance, be composed of a wire mesh with pores small enough to block passage of the beads.

Figure 8:
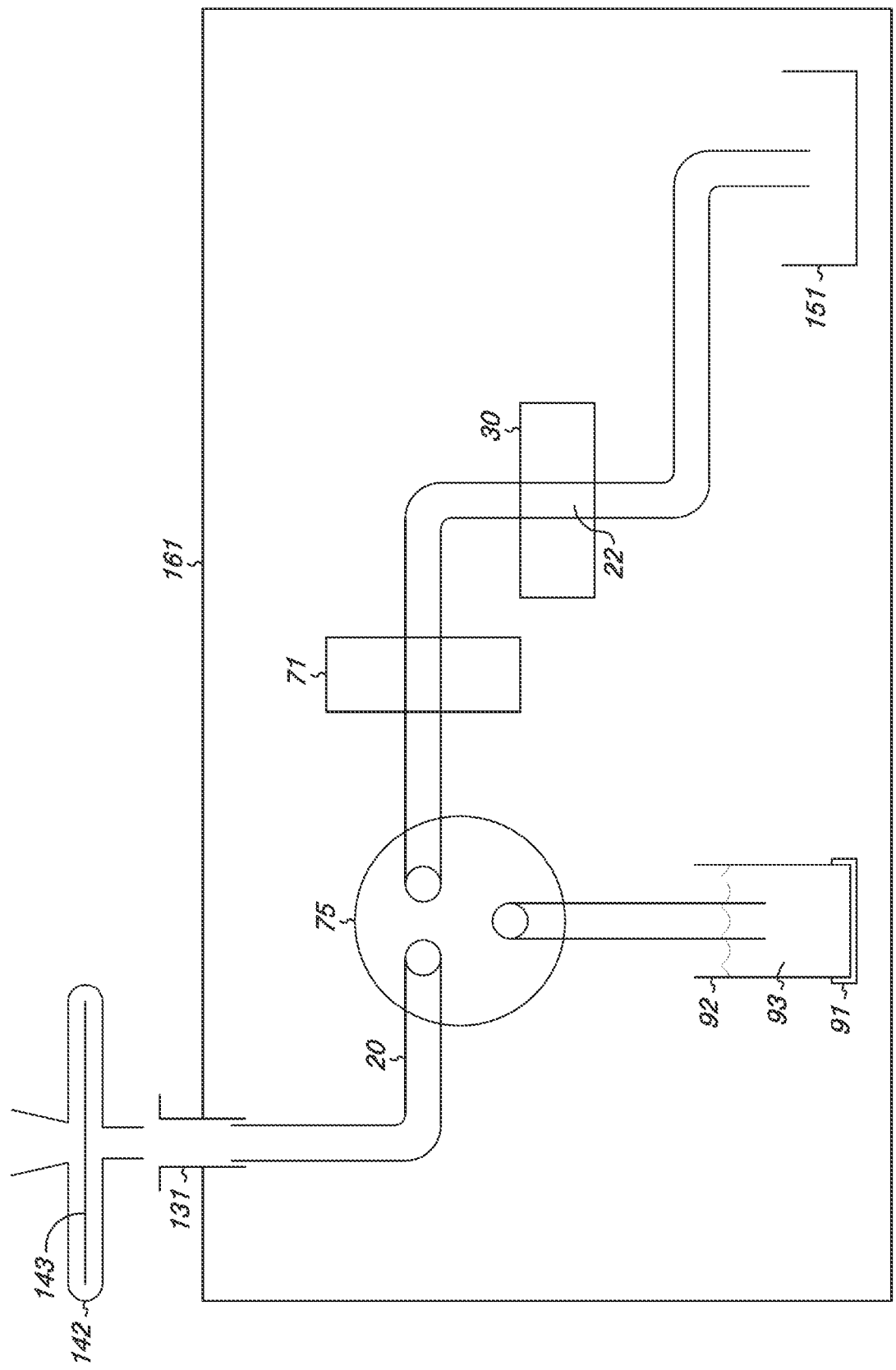
FIG. 8 shows an apparatus for detecting bacteria in a sample.

Another embodiment of the invention provides an apparatus illustrated in FIG. 8. The apparatus 161 in this example includes a port 131 adapted to receive a vessel 142 holding a sample suspected of containing bacterial cells. The vessel 142 in the example shown in FIG. 8 is a filter device that has a fluid-passable filter 143 that has a pore size of less than 1 micron and is impassable to intact bacterial cells. The filter device would have been used to filter a fluid sample as shown above in device 161 in FIG. 8 to generate a testing sample substantially free of eukaryotic cells.

The apparatus 161 also has a passageway 20 in fluid communication with the port and in fluid communication with an assay chamber 22. A light detector 30 is functionally linked to the assay chamber to detect light emitted in the assay chamber.

The apparatus also has a pump 71 functionally linked to the passageway and assay chamber and adapted to pump fluid through the passageway and to the assay chamber.

The apparatus 161 is adapted to pump a lysing fluid 93 from the passageway through the port and the fluid-passable filter of the vessel when the vessel 142 is received on the port 131, to lyse bacteria in the vessel and thereby generate a bacterial lysate containing bacterial ATP in the vessel 142. In FIG. 8, the lysing fluid 93 also contains luciferase and luciferin. The lysing agents in this solution can be detergents, so the pH is close to neutrality and compatible with luciferase and luciferin. We have used BAC-TITER GLO reagent from Promega (Madison, Wis.). This contains a mixture of detergents and luciferin and luciferase. Separate lysing fluids and luciferase/luciferin solutions can also be used.

It has been found that TRITON X-100 at concentrations above 1%, BRIJ, TWEEN detergents other than TWEEN-20, and sodium cholate all lyse bacteria. Trichloroacetic acid, ammonia at high concentration, and sodium hydroxide can also be used to lyse bacteria. In the case of use of acids and bases, it is preferable to neutralize the pH for the luciferase reaction.

In FIG. 8 the lysing fluid 93 is pumped through multiport selection valve 75 to passageway 20 and port 131 and over the filter 143 to lyse bacteria present on the outside of the filter, generating a bacterial lysate fluid in vessel 142. The pump in this example is a bidirectional pump, so after a time suitable to allow bacterial lysis it reverses direction to pump the bacterial lysate fluid, which is also the ATP assay fluid since it contains in this example luciferase and luciferin, back through passageway 20 and multiport selection valve 75 to assay chamber 22 in light detector 30. The light detector monitors light emission from the ATP assay fluid in the assay chamber 22. Thus, the apparatus 161 pumps the bacterial lysate from the vessel through the fluid-passable filter of the vessel into the passageway; contacts the bacterial ATP in the bacterial lysate with luciferase and luciferin to form an ATP assay fluid; and monitors light emission from the ATP assay fluid in the assay chamber.

In some embodiments, the apparatus also contains a waste receptacle 151, and fluid is pumped from the device to the waste receptacle 151.

Thus, in particular embodiments, the apparatus—comprising (a) a port adapted to receive a vessel holding a sample suspected of containing bacterial cells, (b) a passageway in fluid communication with the port and in fluid communication with (c) an assay chamber functionally linked to (d) a light detector to detect light emitted in the assay chamber, and (e) a pump functionally linked to the passageway and the assay chamber and adapted to pump fluid through the passageway and to the assay chamber—further comprises the vessel received on the port.

In other embodiments, the apparatus further comprises (f) a multiport selection valve in fluid communication with the passageway and the lysing chamber, (g) a holding means for receiving a lysing fluid chamber in fluid communication with the multiport selection valve, and (h) a holding means for receiving a waste fluid container in fluid communication with the multiport selection valve.

The devices to separate eukaryotic cells from intact bacterial cells that may be present in a fluid sample to generate a testing sample to test for bacterial cells may also be included in the systems and apparatuses disclosed that perform the steps of lysing the bacterial cells to release bacterial ATP into a fluid to generate a bacterial lysate fluid, contacting the bacterial ATP in the bacterial lysate fluid with an ATP-consuming enzyme to generate an ATP assay fluid in which the enzyme catalyzes a light-producing reaction, and monitoring the enzyme-catalyzed reaction in the ATP assay fluid. In this way fully automated systems and apparatuses are provided that separate intact eukaryotic cells from intact bacterial cells, lyse the bacterial cells to release bacterial ATP, contact the bacterial ATP with an ATP-consuming enzyme to generate an ATP assay fluid in which the enzyme catalyzes a reaction, and monitor the enzyme-catalyzed reaction in the ATP assay fluid. A user merely provides a fluid sample to be tested for bacteria, and the system or apparatus processes the fluid sample to provide a result that indicates the presence or absence of bacteria in the sample, and optionally the quantity of bacteria in the sample if they are present.

Another embodiment of the invention provides an apparatus for determining the presence or absence of bacteria in a sample suspected of containing bacteria. The apparatus includes: (a) a receptacle means for receiving a sample suspected of containing bacterial cells; linked to (b) a means for lysing the bacterial cells to release bacterial ATP into a fluid to generate a bacterial lysate fluid; linked to (c) a means for contacting the bacterial ATP in the bacterial lysate fluid with an ATP-consuming light-producing enzyme to generate an ATP assay fluid in which the enzyme catalyzes a light-producing reaction; linked to (d) a light-detector means for detecting light produced by the enzyme in the ATP assay fluid.

The means for lysing bacterial cells can be a sonication device or bead mill, for instance. But most preferably it is a system of pumps, passageways, and fluid reservoirs for delivering a lysing fluid to the sample suspected of bacteria, such as are described herein, or equivalents thereof.

The means for contacting the bacterial ATP in the bacterial lysates fluid with an ATP-consuming light-producing enzyme can be the same means, or overlapping means, as that for lysing bacterial cells. It is preferably a system of pumps, passageways, and fluid reservoirs for delivering a fluid containing the ATP-consuming light-producing enzyme. The two means are the same and the bacterial lysate fluid and ATP assay fluid are the same if a single solution containing lysing agent(s), luciferase, and luciferin is contacted with intact bacterial cells to lyse the cells and simultaneously contact the bacterial ATP with luciferase.

In some embodiments of this apparatus, the apparatus further comprises a bacteria-separating means for separating intact eukaryotic cells in a fluid sample from intact bacterial cells in the fluid sample to generate a testing sample that is substantially free of eukaryotic cells, wherein the bacteria-separating means is linked to the receptacle means.

Figure 10:
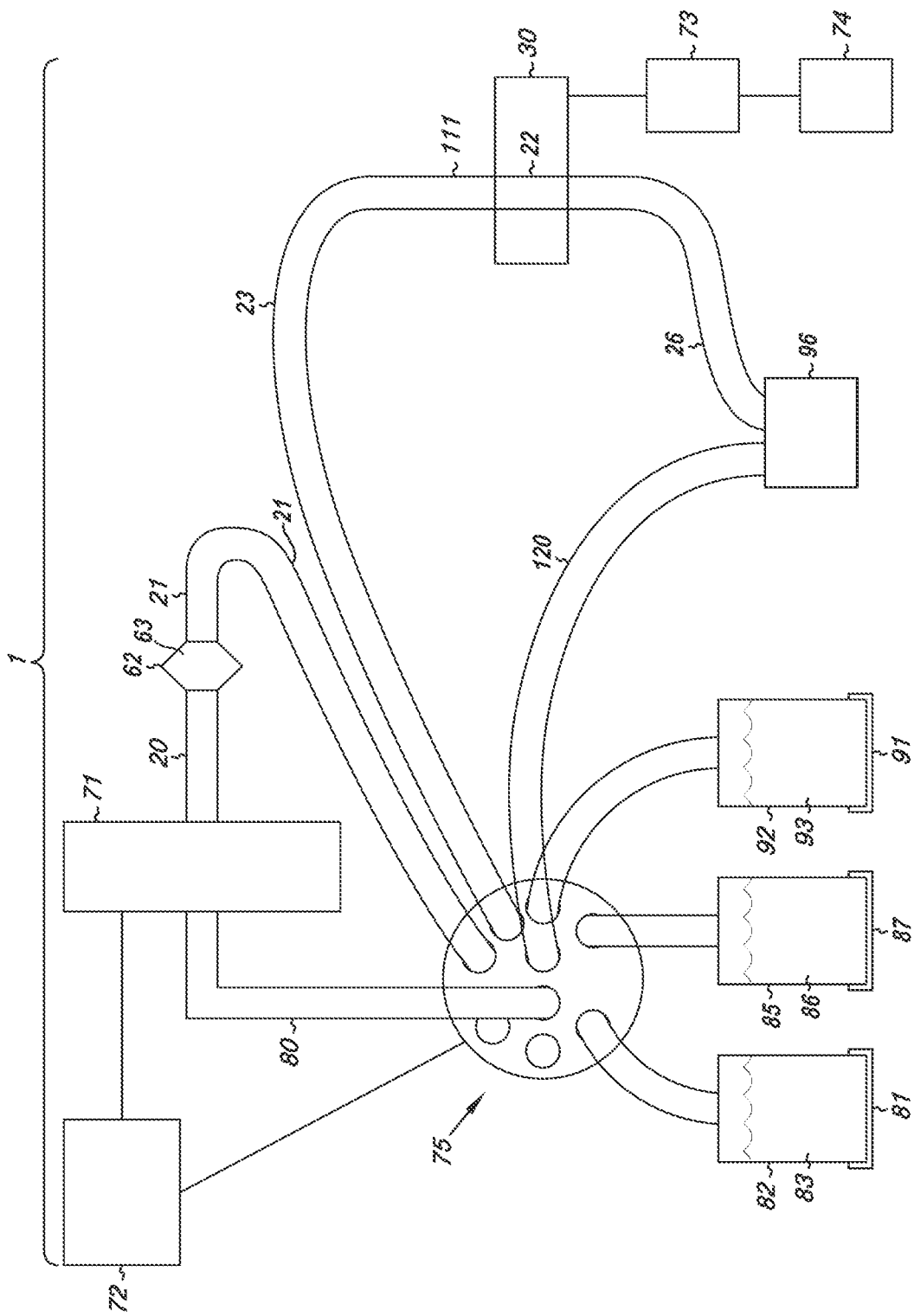
FIG. 10 shows a system of the invention for detecting cells that uses an oxidizing solution to consume extracellular ATP.

FIG. 10 shows another embodiment of a system for detecting cells. In the embodiment shown, 62 is a filter device containing a sample 63 suspected of containing cells, which is a filter on which cells have been trapped. The filter device 62 may be, in one embodiment, the second filter device 142 shown in FIG. 7, that is used to trap bacteria after filtering a fluid sample through a first filter that blocks intact eukaryotic cells. The filter device 62 in the FIG. 10 is held by tubing 20 and 21. The system of FIG. 10 also includes a wash solution reservoir chamber 82 held in a holding means 81 and containing a wash solution 83. In one embodiment, the wash solution 83 is an oxidizing solution effective to consume ATP. A luciferase solution reservoir 92 held by a holding means 91 and containing a luciferase solution 93 is also shown. The solutions held in the reservoirs are linked to a multiport selection valve 75, which outputs the appropriate solution pumped by pump 71 to passages 80 or 120 or 23. Initially, the oxidizing solution 83 is pumped by pump 71 through passage 80 to passage 20 and filter device 62 to oxidize any free ATP in the sample 63. The fluid oxidizing solution continues through passage 21 to multiport selection valve 75, where it is directed through passage 120 to waste reservoir 96. 87 is a holding means holding vessel 85 containing reducing solution 86. The reducing solution 86 is pumped through the multiport selection valve, passageways 80 and 20 to filtering device 62 to reduce oxidant remaining on the sample 63. The reducing solution is pumped through passageway 21 to multiport selection valve 75 to passageway 120 and wash reservoir 96. Then luciferase solution 93 is pumped through the multiport selection valve 75 and the passageways to the filter device 62 containing sample 63. In one embodiment, the luciferase solution contains luciferin and a detergent solution that lyses bacterial cells and is compatible with luciferase activity. Thus, the solution 93 is contacted with bacteria in sample 63 and lyses the bacteria to release ATP. The bacterial lysate continues through passageway 21 to multiport selection valve 75. The multiport selection valve directs the lysate solution containing luciferase and luciferin through passage 23 to assay chamber 22 in light detector 30. Luciferase in the solution 93 consumes ATP to emit light which is detected by the light detector 30. From assay chamber 22, the fluid continues through passageway 26 to waste reservoir 96.

Thus, FIG. 10 shows one embodiment of a system for detecting cells in a sample comprising: (a) a holding means for receiving a device containing a sample suspected of containing cells; (b) a holding means holding a first fluid reservoir chamber containing an oxidizing solution effective to consume ATP; (c) a fluid-tight material forming an assay chamber adapted to receive fluid flow from the device containing a sample suspected of containing bacteria; (d) a light detector functionally linked to the assay chamber to detect light emitted in the assay chamber; and (e) a pump functionally coupled to the first fluid reservoir chamber and to the device containing a sample suspected of containing cells, the pump adapted to pump the oxidizing solution from the first fluid reservoir chamber to the device containing a sample suspected of containing cells to consume free ATP in the sample suspected of containing cells.

The embodiment shown in FIG. 10 also comprises (f) a holding means 91 holding a second fluid reservoir chamber 92 containing a lysis solution 93 effective to lyse cells; and (g) a multiport selection valve 75 in fluid communication with the first fluid reservoir chamber and the second fluid reservoir chamber, the multiport selection valve adapted for transmitting fluid from the first fluid reservoir chamber in one position and the second fluid reservoir chamber in another position; wherein the pump (b) is functionally coupled to the multiport selection valve and the second fluid reservoir chamber and is adapted to pump the lysis solution from the second fluid reservoir chamber to the device containing a sample suspected of containing cells.

Another embodiment of a system for detecting cells comprises (f) a holding means holding a second fluid reservoir chamber containing a lysis solution effective to lyse cells; and (g) a pump functionally coupled to the second fluid reservoir chamber and to the device containing a sample suspected of containing cells, the pump adapted to pump the lysis solution from the second fluid reservoir chamber to the device containing a sample suspected of containing cells to lyse the cells in the sample; wherein pump (g) and pump (e) may be the same pump. Thus, the system does not require a multiport selection valve.

Figure 11:
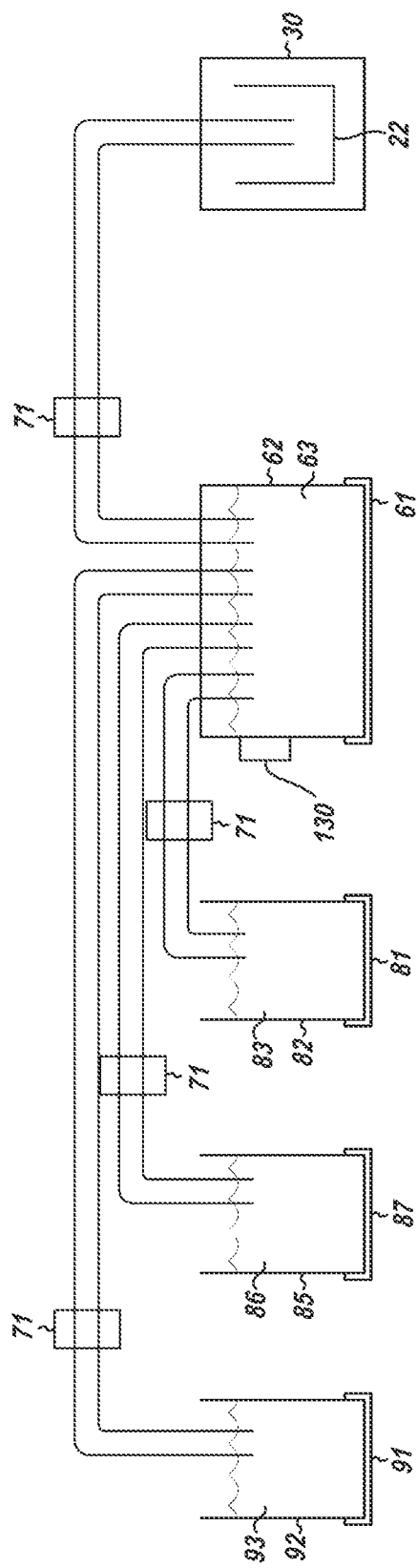
FIG. 11 shows a system of the invention for detecting bacteria that uses a sonicator to selectively lyse eukaryotic cells.

FIG. 11 shows a system for detecting bacteria in a fluid sample comprising: (a) a holding means for receiving a vessel containing a sample suspected of containing bacteria; (b) a sonicator adapted to sonicate the sample suspected of containing bacteria in the vessel; (c) a fluid-tight material forming an assay chamber adapted to receive fluid flow from the vessel containing a sample suspected of containing bacteria; and (d) a light detector functionally linked to the assay chamber to detect light emitted in the assay chamber.

In FIG. 11 receptacle 61 holds sample reservoir vessel 62, which contains a fluid sample 63. An oxidizing solution 83 is held in fluid reservoir 82, which is held by receptacle 81. A reducing glucose solution 86 is held in fluid reservoir 85 on receptacle 87. A luciferin/luciferase/lysing solution 93 is held in fluid reservoir 92 on receptacle 91. A sonicator 130 is functionally coupled to fluid sample reservoir vessel 62 to sonicate fluid sample 63, where fluid sample 63 contains a detergent, to selectively lyse eukaryotic cells in the sample without substantially lysing bacterial cells. After lysing the eukaryotic cells by sonication with detergent (preferably CHAPS), oxidizing solution 83 is pumped into the sample to oxidize ATP. Then a reducing solution 86, which may be a glucose solution, is pumped into the sample reservoir vessel 62 to reduce the oxidant, thereby preventing it from reacting with ATP from bacteria when the bacteria are lysed. Finally, a lysing solution 93 containing agents to lyse bacteria and luciferin and luciferase is pumped to fluid sample reservoir 62 to mix with the sample, lyse bacteria in the sample, and act on bacterial ATP that is released with luciferase to emit light. The fluid sample is then pumped to assay chamber 22 in light detector 30. There light from the reaction mixture is quantified. Pumps 71 act to pump the fluids.

Figure 12:
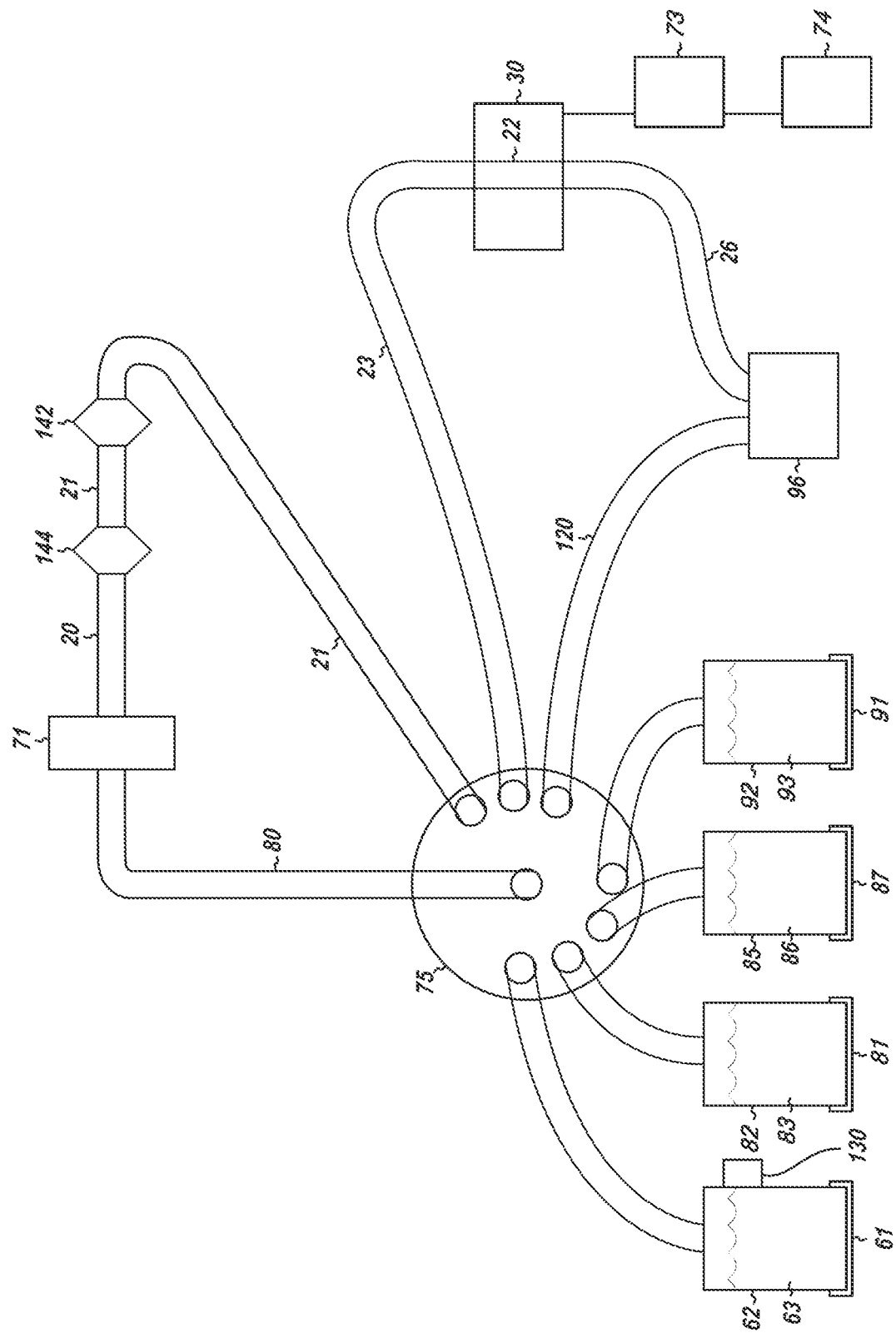
FIG. 12 shows another system of the invention for detecting bacteria that uses a sonicator to selectively lyse eukaryotic cells.

FIG. 12 shows another embodiment where sample reservoir 62 is coupled with sonicator 130. The sonicator 130 sonicates the sample 63 in reservoir 62 to selectively lyse eukaryotic cells in the sample without substantially lysing bacterial cells. The sample with lysed eukaryotic cells can be pumped through multiport selection valve 75 to passageways 80 and 20 to a filter device 144 containing a filter that blocks intact eukaryotic cells and allows bacterial cells to pass through. This filter device is not typically necessary since eukaryotic cells have already been lysed, but it may be useful if small numbers of intact eukaryotic cells survive. Intact bacterial cells are then trapped on the filter in filter device 142 that blocks bacterial cells. This concentrates the bacterial cells. Oxidizing solution 83 may then be pumped through the passageways to filter device 142 to oxidize and inactivate any extracellular ATP in the sample on filter device 142. Reducing solution 86 is then pumped through filter device 142 to react with and inactivate the oxidizing solution. These solutions are pumped further through passageway 21 to multiport selection valve 75, which directs the fluid flow through passageway 120 to waste vessel 96. Finally, a lyse/luciferin/luciferase solution 93 is pumped up through the passageways to filter device 142, where it lyses bacteria on the filter to release bacterial ATP. The bacterial ATP in the bacterial lysate solution is then consumed by luciferase to emit light. The bacterial lysate solution is pumped further through passageway 21 to multiport selection valve 75, which directs the flow to passageway 23 and on to assay chamber 22 in light detector 30. There the light emitted by luciferase consuming ATP is detected and quantified.

Another embodiment of the invention provides an improved optical component in a device for detecting cells (bacterial or eukaryotic). In this embodiment, the assay chamber is placed between a light detector and a concave mirror. Light emitted from the assay chamber that is directed away from the light detector is reflected and focused from the concave mirror back onto the light detector to improve detection. This embodiment of the invention provides a system for detecting cells in a sample comprising: (a) a holding means for receiving a device containing a sample suspected of containing cells; (c) a fluid-tight material forming an assay chamber adapted to receive fluid flow from the device containing a sample suspected of containing cells; (d) a light detector functionally linked to the assay chamber to detect light emitted in the assay chamber; and (e) a concave mirror positioned to reflect light emitted from the assay chamber and concentrate the light onto the light detector.

Figure 13B:
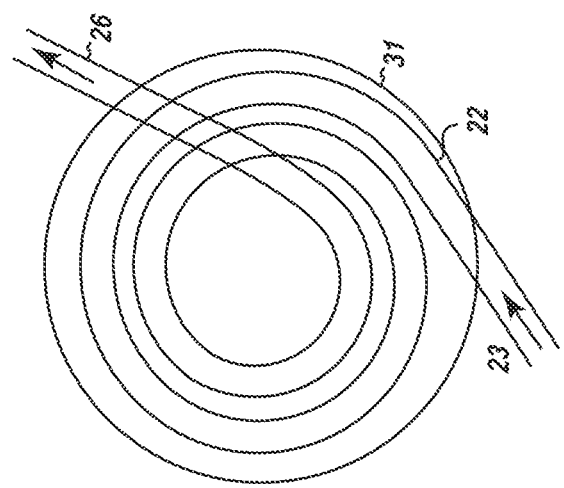
FIG. 13 shows two views of an arrangement of the assay chamber between the light detector and a concave mirror to enhance light detection in panels A and B.
Figure 13A:
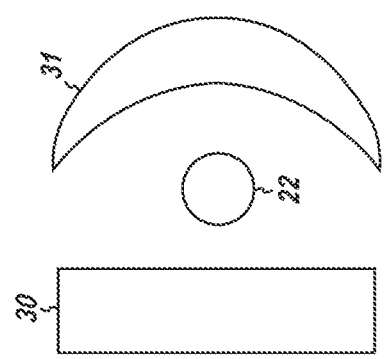

The light detector and mirror arrangement is shown in FIG. 13. Light detector 30, which in one embodiment is a photomultiplier tube, is shown in panel A. Assay chamber 22, which may be a section of tubing through which fluid flows, is shown in panel A positioned on the face of light detector 30. On the opposite side of assay chamber 22 is a concave mirror 31, which reflects and focuses light from the assay chamber back onto the light detector. In one preferred embodiment, the assay chamber 22 is a coiled tube, i.e., it is section of tubing that is arranged in a coil on the face of the mirror 31. This is shown in panel B of FIG. 13. In FIG. 13, fluid flow enters assay chamber 22 from passageway 23 and exits through passageway 26. The coiled tube may be any suitable shape.

Another embodiment provide a method of detecting cells in a liquid sample comprising: (a) concentrating cells in a liquid sample and removing the cells from liquid medium of the sample by a process comprising: (i) passing the liquid sample through a filter that blocks the cells; or (ii) contacting the liquid sample with a support surface that binds the cells; or (iii) centrifuging the sample for a time and at a speed sufficient to pellet the cells; (b) contacting the cells removed from the liquid medium with a volume of rich liquid growth medium smaller than the removed liquid medium volume; (c) incubating the cells in the rich liquid growth medium for a time and under conditions effective to amplify the cells; (d) lysing the cells to release cellular ATP into a fluid to generate a cell-lysate fluid; and (e) detecting ATP in the cell-lysate fluid. In this embodiment, it is possible to detect even lower numbers of bacterial or eukaryotic cells than without transferring the cells into rich medium and amplifying them. The cells are amplified before detecting them. And by concentrating the cells before placing them in rich medium, the cells are able to get into logarithmic growth faster than and multiply with a shorter doubling time than they could if maintained in a larger volume with a lower concentration of cells.

In one embodiment, bacterial cells are detected by passing a 1-ml liquid sample through a 0.2 micron pore size filter, and then pumping 100 microliters of tryptic soy broth plus glucose onto the cells on the filter. The rich medium can be pumped back and forth to agitate and mix the cells and better aerate them. That appears to improve growth. We have found that with this method cells reach logarithmic growth in just one hour. Incubation for a further 2 hours after the cells reach logarithmic growth may allow 4 or more doublings of cell numbers. Four doublings of cell number is a 16-fold increase in cell numbers, so this can substantially increase sensitivity and allow detection of smaller numbers of starting cells.

In other embodiments, the liquid sample is centrifuged for a time and at a speed sufficient to pellet the cells, and the pellet of cells is resuspended in rich growth medium and incubated. And in another embodiment the liquid sample is contacted with a support surface that binds the cells in the sample, the liquid medium of the liquid sample is removed from the binding surface, and the cells are then contacted with rich liquid growth medium and incubated to amplify the cells. The cells can be amplified when bound to the support surface, or they can be removed from the support surface to incubate and amplify the cells.

Tryptic soy broth with glucose is found to be a suitable rich growth medium for almost all species of bacteria. Cells can be incubated aerobically or anaerobically. To detect anaerobic bacteria, in some embodiments it is useful to purge the medium and the device tubing with nitrogen or argon to remove oxygen and to maintain the liquid growth medium in anaerobic conditions during the incubation. It may also be desirable in certain embodiments to add thioglycolate or another reductant to the growth medium to amplify anaerobic bacteria.

The method allows amplifying cells in a rather short period of time to increase sensitivity. In particular embodiments, the cells are incubated in the rich liquid growth medium for less than 24 hours, less than 12 hours, less than 8 hours, less than 6 hours, less than 4 hours, less than 3 hours, or even less than 2 hours.

In particular embodiments, the step of incubating the cells in rich liquid growth medium comprises agitating the liquid medium during the incubation period. The agitation can be with pumping the growth medium back and forth over the filter or over the binding surface in the devices described herein.

In general, we have found that one growth medium and one growth condition works well for almost all species of bacteria. But in some cases, different incubation conditions can be desirable to allow all possible species of cells to multiply. Thus, in particular embodiments, the method comprises before the incubating step dividing the cells in the sample into two groups and incubating the two groups of cells in rich liquid medium separately in different conditions. The cells can be divided into two groups in different ways that will be apparent to one of skill in the art. For instance, the liquid sample containing the cells can be divided in two and the two resulting liquid samples can be processed separately. After concentrating the cells and separating them from liquid medium of the sample, the cells may also be resuspended in the growth medium and the growth medium divided into two volumes, and cells in the two volumes incubated and amplified separately.

In one embodiment, one group of cells is incubated aerobically, and one group is incubated anaerobically. Other conditions that may vary between the two groups can be the growth medium or the temperature. In general, a preferred temperature for amplification is 37° C.

The invention will now be illustrated by the following non-limiting examples.

EXAMPLES

Example 1

Assay of Platelet Concentrate for Bacterial Contamination Using Bacteria-Binding Beads The assay procedure used was as follows.

1. A 1.0 ml platelet concentrate sample was pumped bidirectionally over a 40 microliter packed bead column of GenPoint BUG TRAP C-version beads (GenPoint, Oslo, Norway) for 60 seconds.

2. The column was flushed with 250 microliters of wash buffer, which was Hank's balanced salt solution (0.185 g/l $CaCl_2$, 0.2 g/l $MgSO_4$, 0.4 g/l KCl, 0.06 g/l $KH_2PO_4$, 8 g/l NaCl, 0.048 g/l $Na_2HPO_4$, 1.5 g/l dextrose anhydrous, 15.7 g/l dextrose monohydrate, 4.77 g/l HEPES, 1.365 g/l $NaH_2PO_4$).

3. Forty microliters of 0.1% trichloroacetic acid in water heated to 60° C. was bidirectionally passed over the column for 10 seconds to create a bacterial lysate fluid.

4. A luciferin-luciferase solution (10 microliters, containing 0.2 µg luciferase, 2 µg luciferin, in 50 mM sodium phosphate pH 7.5) was mixed with the bacterial lysate fluid by sequential injection analysis and mixing of the fluid zones (Global FIA, Fox Island, Wash.) to form an ATP assay fluid that was passed in front of a luminescence detector (photon counter, from Electron Tubes, England) to detect the burst of light.

One platelet concentrate bag was divided into four samples, each contained in a PL732 bag. Each bag was inoculated with 10 CFU/ml of *Escherichia coli, Pseudomonas aeruginosa, Staphylococcus aureus*, or *Serratia marcescens*. Four control bags were not inoculated with bacteria. After 36 hours at room temperature, 5 ml from each bag was transferred to BACT/ALERT culture bottles for automated culture system bacterial load detection. Using the BACT/ALERT, 5 ml of each sample was inoculated into standard aerobic, standard anaerobic, activated charcoal aerobic, and anaerobic bottles.

A 1.0 ml sample of each bag was also tested as described above for bacterial ATP.

The results are shown in Table 1.

TABLE 1

| Strain | Inoculum (cfu/ml) | Incubation Time (hours) | BacT (cfu/ml) | Relative Light Units |
|---|---|---|---|---|
| E. coli | 10 | 36 | 517 | 1,476,200 |
| Pseudomonas | 10 | 36 | 772 | 1,807,426 |
| Staphylococcus | 10 | 36 | 415 | 1,267,845 |
| Serratia | 10 | 36 | 546 | 1,296,966 |
| E. coli | 0 | Post collection | Not detectable | 650 |
| Pseudomonas | 0 | Post collection | Not detectable | 713 |
| Staphylococcus | 0 | Post collection | Not detectable | 953 |
| Serratia | 0 | Post collection | Not detectable | 733 |

Example 2

Device to Separate Eukaryotic Cells from Bacteria and Concentrate Bacteria

A 5-ml syringe was linked in series to a 25-mm diameter 5-micron pore size ACRODISC SUPOR membrane filter and then a 15-mm diameter 0.2-micron pore size ACRODISC SUPOR membrane filter. The syringe and filters were linked by their luer lock connectors in the order of syringe-5 micron filter-0.2 micron filter. Platelet concentrate was tested for processing with the device. The platelet concentrate (3 ml) was loaded in the syringe and then forced through the two filters. It is expected the first filter would remove platelets and other eukaryotic cells, and the second filter would stop and concentrate bacteria. The filtrate from the first filter, a 5-micron pore size filter, was examined for platelets and other eukaryotic cells by coulter counting and microscopic examination. It was found that no platelets or other eukaryotic cells passed through the first filter. This was a bit surprising in that the nominal pore size of the first filter was 5 microns and platelets have a diameter of approximately 3 microns.

Example 3

Computer-Controlled Bacterial Detection Device

A device essentially as shown in FIG. 8 was built. A model C25Z multiport selection valve (Valco Instruments Co. Inc., Houston, Tex.; www.vici.com) was linked by narrow-bore tubing with a wash solution reservoir (70% isopropyl alcohol) and a lysis/luciferase/luciferin solution reservoir (BACTI-TER-GLO reagent, Promega, Madison, Wis.; www.promega.com). The multiport valve was also linked to a MILIGAT pump (Global FIA, Inc., Sag Harbor, Wash.; www.globalfia.com). The light detector was a photomultiplier tube model P25232 from Electron Tubes, Inc. (Rockaway, N.J.; www.electrontubes.com). The valve, pump, and photomultiplier were controlled by a TPC-60S touch panel PC with WINDOWS XP software. Results from the photomultiplier tube were also displayed on the PC display.

The device also included a port 131 as shown in FIG. 8, on which a 0.2 micron filter containing bacteria on the filter's outer surface could be mounted.

In one embodiment, the device was programmed to pump 150 µl of the lyse/luciferin/luciferase solution through the sample port and onto the filter to lyse the bacteria. The solution was left on the filter for 30 seconds. Then the pump direction was reversed to pump the 150 µl of fluid from the filter to the assay chamber in the photomultiplier tube. Counting proceeded for 20 seconds. Then the solution was pumped to a waste container. The program then called for pumping 2.5 ml of the isopropyl alcohol solution through the lines to clean the lines.

Example 4

Assays for Bacterial Contamination Using the Device of Example 3

Samples of plasma were spiked with particular species of bacteria. Three ml of the plasma was then incubated with 60 µl of GenPoint BUG TRAP C-version beads (GenPoint, Oslo, Norway) for 5 minutes. The sample was then filtered through a 5-micron pore size ACRODISC SUPOR membrane to trap and concentrate the beads. The filter with the beads on it was loaded on the port of the device described in Example 3. The program described in Example 3 was executed to lyse the bacteria on the beads and quantify luminescence from the solution. The results are shown below in Table 2.

TABLE 2

Comparison of Relative Light Units (RLU) with number of bacteria determined by quantitative culture in plasma samples.

| Organism | RLU | cfu/ml |
|---|---|---|
| Plasma alone | 23,000 | 0 |
| Escherichia coli | 286,000 | 10,800 |
|  | 190,000 | 1,080 |
| Enterobacter cloacae | 305,000 | 3,700 |
|  | 216,000 | 370 |
| Klebsiella oxytoca | 197,000 | 6,600 |
|  | 146,000 | 600 |
| Pseudomonas aeruginosa | 315,000 | 7,700 |
|  | 222,000 | 770 |
| Bacillus subtilis | 234,000 | 1,300 |
|  | 186,000 | 130 |
| Staphylococcus aureus | 315,000 | 11,400 |
|  | 222,000 | 1,140 |
| Staphylococcus epidermidis | 286,000 | 10,600 |
|  | 190,000 | 1,060 |
| Serratia marcescens | 210,000 | 5,400 |
|  | 86,000 | 540 |
| Bacillus cereus | 176,000 | 1,500 |
|  | 174,000 | 150 |
| Corynebacterium species | 87,000 | 340 |
|  | 54,000 | 34 |
| Streptococcus pyogenes | 13,500 | 3,700 |
|  | 14,500 | 370 |
| Streptococcus viridans | 11,000 | 14,600 |
|  | 11,000 | 1,460 |
| Clostridium perfringens | 86,500 | unknown |
| Propionibacterium acnes | 68,000 | unknown |

Only the two *Streptococcus* species gave luminescence similar to background and thus were not detected by this luminescence detection method. The inventor believes that this is because the cells were not adequately lysed, and that incubation in the same lysis reagent for longer than the 30 seconds used in this protocol would allow detection of *Streptococcus*.

Figure 9:
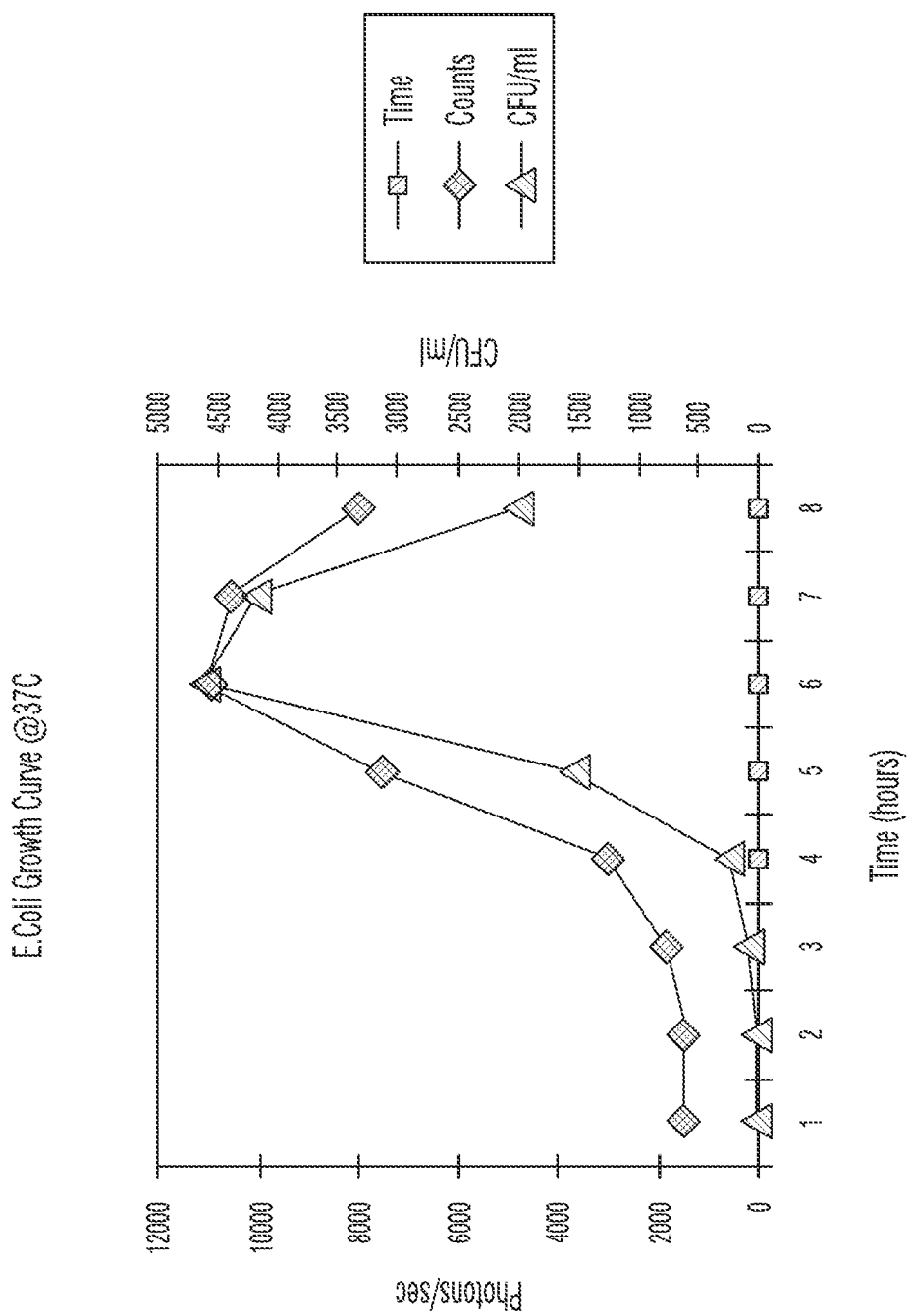
FIG. 9 shows a growth curve of bacteria in platelet concentrate as determined by a method of the invention yielding relative light units as a measure of bacteria amount, as compared to a growth curve determined by plating the platelet concentrate to measure bacterial colony forming units.

Next a bag of platelet concentrate was spiked with *E. coli* at 10 cfu/ml and incubated at 37° C. Samples were taken every 1 hour and assayed for bacteria by the method described above in this Example, yielding relative light units, or plated quantitatively to determine cfu/ml. The results are shown in FIG. 9. The results in relative light units determined with the present device closely matched the determination of colony forming units by plating.

These results show that a broad range of bacteria, including gram positives, gram negatives, and anaerobic bacteria, can be detected by the present methods with a sensitivity of less than 1000 cfu/ml, and usually less than 100 cfu/ml.

Example 5

Assay for Bacteria in Urine

In this assay, urine samples were spiked with 4,000 cfu/ml of various species of bacteria and assayed. One ml of each sample was mixed with TRITON X-100 to a final concentration of 0.1% TRITON X-100 and then passed in series through a 5 micron filter and then a 0.2 micron filter. The 5 micron filter filters most of the intact eukaryotic cells. The 0.2 micron filter with trapped bacterial cells was placed in a device as shown in FIG. 10. Five ml of 0.025 M $NaIO_4$ solution was passed over the filter at 0.6 ml/sec to oxidize any ATP from lysed eukaryotic cells, and then 5 ml of 0.5 M glucose was passed over the filter at 0.6 ml per sec to consume the oxidant. BACTITER-GLO lysis/luciferase/luciferin solution (150 µl) was transferred to the filter and left with the bacterial sample on the filter for 30 seconds to lyse bacteria. The lysis solution containing ATP from lysed bacteria and luciferase and luciferin was transferred to the photo detector and relative light emission was measured. The results are shown in Table 3 below.

TABLE 3

Relative Light Units (RLU) detected from urine samples spiked with $10^4$ CFU/ml of various species of bacteria.

| Organism | Counts |
| --- | --- |
| Urine control | 108,286 |
| *Clostridium* sp. | 2,367,354 |
| *Pseudomonas* sp. | 986,587 |
| *Serratia* sp. | 886,364 |
| *Staphylococcus epidermidis* | 3,465,340 |
| *Escherichia coli* | 2,207,533 |
| *Staphylococcus aureus* | 772,508 |
| *Klebsiella* sp. | 1,345,381 |
| *Propionibacterium acnes* | 3,253,989 |
| *Bacillus cerus* | 9,253,989 |
| *Enterobacterium cloacae* | 12,563,767 |
| *Streptococcus pyogenes* | 899,248 |
| *Streptococcus viridans* | 1,772,002 |

REFERENCES

1. Epstein J S, Williams A E, Biswas R, Vostal J. *FDA Update at the AABB Annual Meeting* Oct. 15, 2001 2001.
2. Morrow J F, Braine H G, Kickler T S, Ness P M, Dick J D, Fuller A K. Septic reactions to platelet transfusions. A persistent problem. *JAMA*. 1991; 266(4):555-558.
3. Barrett B B, Andersen J W, Anderson K C. Strategies for the avoidance of bacterial contamination of blood components. *Transfusion*. March 1993; 33(3):228-233.
4. Dumont L. *Bacterial Contamination of Platelet Components*. Lakewood: COBE BCT Inc.; 1996.
5. Mitchell K-M T, Brecher M E. 1999. *Transfusion Medicine Reviews* 13:132-144.
6. Chaney R., et al. 1999. *Transfusion Medicine* 9:177-188.
7. Hanna B A. 1986. *Methods in Enzymology* 133:22-27.
8. Nilsson L E et al. 1989. *J. Bioluminescence and Chemiluminescence* 3:101-104.
9. Stanley P E 1989. *J. Bioluminescence and Chemiluminescence* 4:375-380.
10. Lundin A, Thore A. 1975. *Applied Microbiology* 30:713-721.
11. Ruzicka J, Hansen E H. 1981. *Flow Injection Analysis*. J. Wiley and Sons.
12. Karlberg B, Pacey G E. 1989. *Flow Injection Analysis: A Practical Guide*. Elsevier.
13. Valcarcel M and Luque De Castro M D, *Flow-Injection Analysis. Principles and Applications*. John Wiley & Sons, New York.
14. U.S. Pat. No. 6,613,579.
15. U.S. Pat. No. 6,716,391.
16. Lemasters J J, Hackenbrock C R. 1979. *Meth. Enzymol.* 56:530-544.
17. Higashi T, et al. 1985. *Thrombosis and Haemostasis* 53:65-69.

All patents, patent documents, and other references cited are hereby incorporated by reference.

What is claimed is:

1. A method of detecting cells in a sample comprising:
   (a) consuming extracellular ATP in a sample suspected of containing cells by contacting the sample with an oxidizing agent; followed by
   (b) removing the oxidizing agent from cells in the sample (i) by consuming the oxidizing agent by contacting the oxidizing agent with a reductant or (ii) by separating the cells from the oxidizing agent;
   (c) lysing cells in the sample to release cellular ATP into a fluid to generate a cell-lysate fluid; and
   (d) detecting ATP in the cell-lysate fluid.

2. The method of claim 1 wherein the oxidizing agent is periodate.

3. The method of claim 1 wherein the method is a method of detecting bacterial cells in a sample containing eukaryotic cells and suspected of containing bacterial cells; wherein the method comprises before step (a) selectively lysing eukaryotic cells in the sample without substantially lysing bacterial cells in the sample.

4. The method of claim 3 wherein the method further comprises before step (c) separating intact eukaryotic cells from intact bacterial cells, wherein step (c) comprises lysing bacterial cells in the sample to release bacterial ATP into a fluid to generate a bacterial lysate fluid.

5. The method of claim 4 wherein the step of separating intact eukaryotic cells from intact bacterial cells comprises filtering the sample through a filter that blocks the eukaryotic cells and allows the bacterial cells to pass through.

6. The method of claim 4 wherein the step of separating intact eukaryotic cells from intact bacterial cells comprises contacting the sample with a support surface that binds bacterial cells and does not bind eukaryotic cells.

7. The method of claim 4 wherein the step of separating intact eukaryotic cells from intact bacterial cells comprises centrifuging the fluid sample at a speed and for a time such that eukaryotic cells substantially pellet and bacterial cells substantially remain suspended in the fluid sample.

8. The method of claim 4 wherein the sample is a blood product comprising platelets, and the step of separating intact eukaryotic cells from bacterial cells comprises clotting the blood product, and removing fluid from the clot.

9. The method of claim 1 wherein step (d) comprises contacting ATP in the bacterial lysate fluid with luciferin and luciferase and detecting light.

* * * * *